(12) United States Patent
Knox

(10) Patent No.: US 11,890,425 B2
(45) Date of Patent: Feb. 6, 2024

(54) MODULAR PANEL BEDDING SYSTEM

(71) Applicant: Gregory Knox, Los Angeles, CA (US)

(72) Inventor: Gregory Knox, Los Angeles, CA (US)

(*) Notice: Subject to any disclaimer, the term of this patent is extended or adjusted under 35 U.S.C. 154(b) by 433 days.

(21) Appl. No.: 17/246,595

(22) Filed: May 1, 2021

(65) Prior Publication Data

US 2022/0347426 A1 Nov. 3, 2022

(51) Int. Cl.
*A61M 21/02* (2006.01)
*A47G 9/02* (2006.01)
(Continued)

(52) U.S. Cl.
CPC .......... *A61M 21/02* (2013.01); *A47C 21/022* (2013.01); *A47C 21/042* (2013.01);
(Continued)

(58) Field of Classification Search
USPC ............................................................ 5/421
See application file for complete search history.

(56) References Cited

U.S. PATENT DOCUMENTS

| 2,624,893 A | 1/1953 | Harris |
| 3,148,388 A | 4/1964 | Espersen |

(Continued)

*Primary Examiner* — Justin C Mikowski
*Assistant Examiner* — Adam C Ortiz

(57) ABSTRACT

The present disclosure is directed to a bedding panel system comprising a bottom or fitted sheet with embedded channels throughout such that at least one or more modular top panels and cushions can be attached to create physical sleep chamber spaces and thus independent "sleep zones" for multiple occupants on a single mattress. A bedding panel system can have dimensions to fit any size mattress. Fitted sheet, modular panels and cushions can include several layered components with comfort or utility features that are customizable for each sleep chamber space. Top, middle and bottom layers of fitted sheet, modular panels and cushions may be comprised of various fabrics and materials desirable for sleep comfort. Middle layers of fitted sheet and modular panels can include items such as foam or gel padding, moisture resistant barriers, biometric sensors for measuring physical health and sleep quality, and hardware for heating and cooling. Customized foot panel compartments comprised of specialized materials and electronic components can also be attached to fitted sheet for elevated comfort in the foot box. Similar materials and cushion components may comprise headrest components designed for the head box sleep section. Bedding panel system components can be embedded with channels, arranged in cross, crisscross and diagonal patterns, containing reinforced holes spaced symmetrically throughout to accommodate different configurations for modular panel and cushion installations with one or more fitted sheets. Bedding panel system component may be fastened together using a variety of material and hardware anchor combinations to enable ease of component connections, sleep comfort, and convenience of occupant access to sleep zones. Similar to modular panel configurations, anchor systems allow cushions, pillows, pillow cases and headrests to connect with fitted sheet to ensure that all sleep components materials remain intact and in place for the duration of the occupants sleep session.

19 Claims, 18 Drawing Sheets

(51) Int. Cl.
    *A47C 21/02*      (2006.01)
    *A47C 21/04*      (2006.01)
    *A61M 21/00*      (2006.01)

(52) U.S. Cl.
    CPC .......... *A47C 21/048* (2013.01); *A47G 9/0246* (2013.01); *A61M 2021/0027* (2013.01); *A61M 2021/0044* (2013.01); *A61M 2021/0066* (2013.01); *A61M 2205/3303* (2013.01); *A61M 2205/3372* (2013.01); *A61M 2205/3375* (2013.01); *A61M 2205/50* (2013.01)

(56) References Cited

U.S. PATENT DOCUMENTS

| | | | |
|---|---|---|---|
| 3,179,958 A | 4/1965 | Carris | |
| 3,570,026 A | 3/1971 | Allison | |
| 3,694,832 A | 10/1972 | Jamison | |
| 3,832,743 A | 10/1974 | Smith | |
| 4,241,466 A | 12/1980 | Mendyk | |
| 4,651,371 A | 3/1987 | Hahn | |
| 4,653,131 A | 3/1987 | Diehl | |
| 4,727,608 A | 3/1988 | Joyce | |
| 4,979,251 A | 12/1990 | Lazar | |
| 5,003,655 A | 4/1991 | Kafai | |
| 5,084,929 A | 2/1992 | Staudinger | |
| 5,161,276 A | 11/1992 | Hutton et al. | |
| 5,231,717 A | 8/1993 | Scott et al. | |
| 5,287,573 A | 2/1994 | Ritacco | |
| 5,287,574 A | 2/1994 | Kardell et al. | |
| 6,061,851 A | 5/2000 | Crowell | |
| 6,098,219 A | 8/2000 | Milber | |
| 6,185,766 B1 | 2/2001 | Farrugia | |
| 6,854,139 B2 | 2/2005 | Lamy | |
| 6,859,962 B2 | 3/2005 | Diak/Ghanem | |
| 6,892,404 B2 | 5/2005 | Harbin et al. | |
| 7,051,387 B1 | 5/2006 | Yoder et al. | |
| 7,124,455 B2 | 10/2006 | Demarco et al. | |
| 7,249,389 B2 | 7/2007 | Russell | |
| 7,398,570 B2 | 7/2008 | Seago | |
| 7,487,560 B2 | 2/2009 | McGrath et al. | |
| 7,608,041 B2 | 10/2009 | Sutton | |
| 8,336,137 B2 | 12/2012 | Aprile et al. | |
| 8,402,580 B2 | 3/2013 | Walvius et al. | |
| 8,627,521 B2 | 1/2014 | Rowson et al. | |
| 8,689,373 B2 | 4/2014 | Caines | |
| 8,973,183 B1 | 3/2015 | Palashewski et al. | |
| 9,510,698 B1 | 12/2016 | Krotova | |
| 9,694,156 B2 | 7/2017 | Franceschetti et al. | |
| 9,981,107 B2 | 5/2018 | Franceschetti et al. | |
| 10,105,092 B2 | 10/2018 | Franceschetti et al. | |
| 10,285,518 B1 | 5/2019 | Nekhala | |
| 10,368,654 B2 | 8/2019 | Sopher | |
| 10,610,034 B2 | 4/2020 | Sturgeon et al. | |
| 10,682,263 B2 | 6/2020 | Heil et al. | |
| 10,716,512 B2 | 7/2020 | Nunn et al. | |
| 10,729,255 B2 | 8/2020 | Erko et al. | |
| 10,792,461 B2 | 10/2020 | Franceschetti et al. | |
| 10,932,585 B1 | 3/2021 | Sopher | |
| 11,206,929 B2 | 12/2021 | Palashewski et al. | |
| 11,666,284 B2 | 6/2023 | Franceschetti et al. | |
| 2007/0000053 A1 | 1/2007 | Yang | |
| 2009/0172881 A1 | 7/2009 | Peterson | |
| 2009/0313757 A1 | 12/2009 | Walsh-Barltrop | |
| 2010/0304632 A1* | 12/2010 | De Meulemeester | B32B 5/26 428/221 |
| 2011/0010249 A1 | 1/2011 | Oexman et al. | |
| 2011/0302716 A1* | 12/2011 | Battaglia | A47G 9/02 5/493 |
| 2014/0359939 A1 | 12/2014 | Carlitz | |
| 2016/0015314 A1 | 1/2016 | Dusanter et al. | |
| 2016/0213309 A1 | 7/2016 | Sannholm et al. | |
| 2019/0201267 A1 | 7/2019 | Demirli et al. | |
| 2019/0350376 A1* | 11/2019 | Kittaneh | A47C 31/105 |
| 2020/0230008 A1* | 7/2020 | Newham | A61B 5/6894 |
| 2020/0405240 A1 | 12/2020 | Palashewski et al. | |

\* cited by examiner

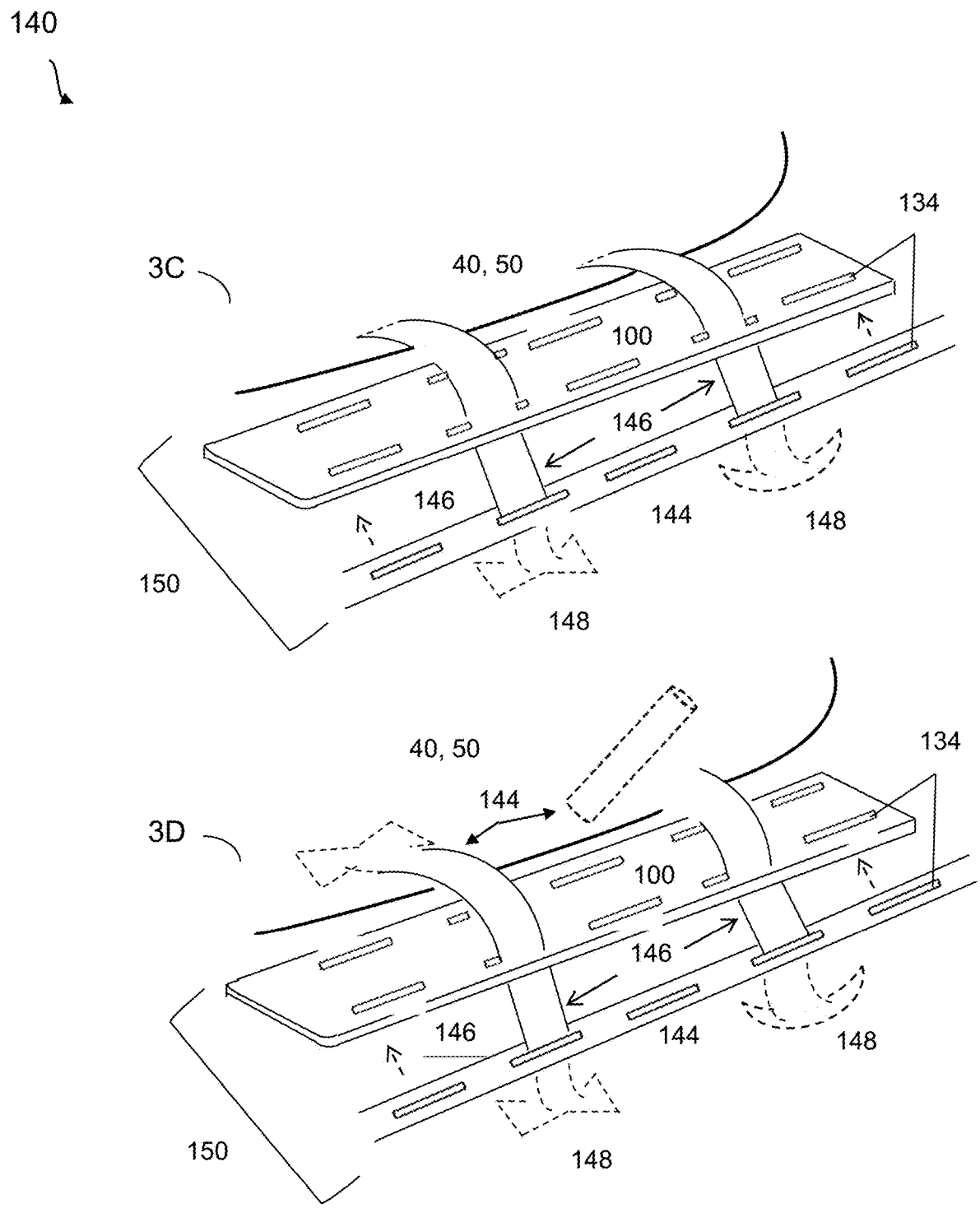
FIGURE 3C-D

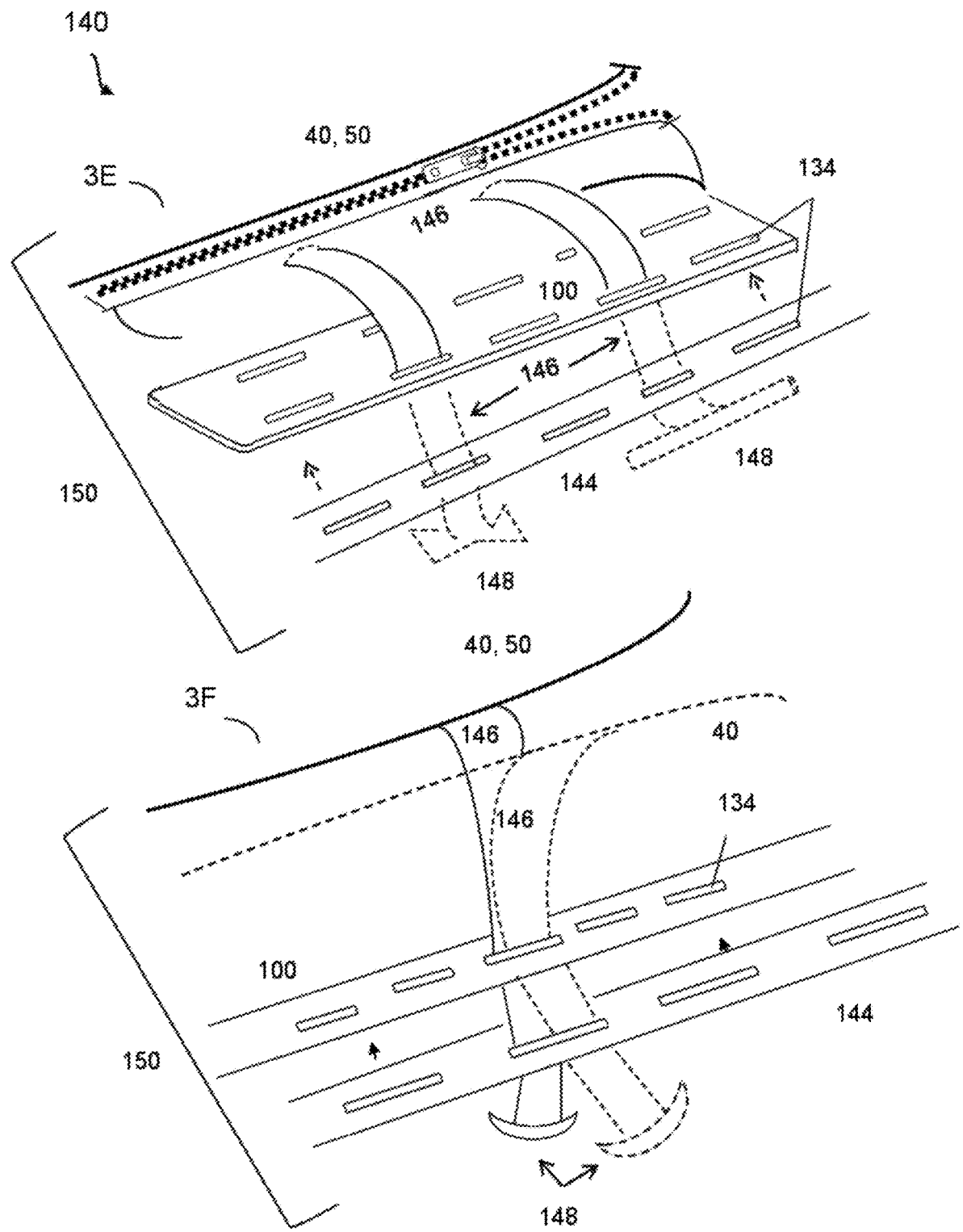
FIGURE 3E-F

500

530

532

| Control Unit/API ||||||| 
|---|---|---|---|---|---|---|
| Bed # Size | Configuration | Sensor System | Comfort | Devices | Technology | User Data |
| #1 King | 4 Zones: (3 Vertical, 1 Horizontal) | Z1, Z2, Z3, Z4 | Z1, Z2, Z3 | Air Quality, Thermostat, Microphone, Speakers | Panels (Z1, Z3) Sacks (Z4) Cloud Access Local Ai | Z1, Z4 |
| #2 Queen | 2 Zones: 2 Horizontal | Z1 | Z1 | Thermostat | Panels | |

516      518

| Users | Bed/Zone | Technology | Preference Data | Sleep Quality Data | Sleep History | Factors |
|---|---|---|---|---|---|---|
| Jeff | Bed #1 Zone 1 | Fitted Sheet | Y | <u>Strong</u><br>• Routine<br>• Pattern<br>• Biometrics<br>• Behaviors | • Time<br>• Stages<br>• Conditions<br>• Events<br>• Biometrics<br>• Behaviors<br>• Charts | • Location<br>• Weather<br>• Seasonal<br>• Med Issue<br>• Stress<br>• Diet |
| Sharon | Bed #1 Zone 2 | Fitted Sheet & Panel | Y | <u>Qualified</u><br>• Routine<br>• Pattern<br>• Biometrics | • Time<br>• Stages<br>• Conditions<br>• Events<br>• Biometrics<br>• Charts | • Location<br>• Partner |
| Guest #1 | Bed #2 Zone 1 | Fitted Sheet | N | <u>None</u> | | |
| Mike | Bed #2 Zone 2 | Sack | N | <u>Limited</u><br>• Routine<br>• Pattern | • Time<br>• Stages<br>• Biometrics<br>• Charts | • Location<br>• Med Issue |

| | | | | Sleep Experience | | |
|---|---|---|---|---|---|---|
| User | Sleep Quality (1 week) | Accuracy | Charts | Behaviors | Factors | Notifications |
| Francis | Poor | 67% | Day Week Month Year | Snoring<br><br>Stress<br><br>Low REM | <u>Negative Sleep Habits</u><br><br>• Temperature<br>• Age<br>• Illness | • Biometrics<br>• Proximity<br>• Activity Level<br>• Audible |
| Debbie | Fair | 39% | Day Week Month Year | Moderate REM<br><br>Disrupted Sleep | <u>Neutral Sleep Habits</u><br><br>• Partner<br>• Sleep Stress<br>• Obesity | • Biometrics<br>• Proximity<br>• Audible<br>• IoT sensor |
| Kate | Excellent | 95% | Day Week Month Year | High REM | Positive Sleep Habits | • Biometrics<br>• Toy Monitor |
| Sam | Good | 82% | Day Week Month Year | Moderate REM | <u>Neutral Sleep Habits</u><br><br>• Snoring<br>• Stress | • Biometrics<br>• Proximity<br>• Audible |

FIGURE 9

MODULAR PANEL BEDDING SYSTEM

COPYRIGHT NOTICE

A portion of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

TECHNICAL FIELD

The present application relates generally to bedding materials and methods for improving sleep quality, and more specifically, to systems and methods for providing customized sleep experiences for multiple individuals sharing a single bed.

BACKGROUND

The mattress industry is one of the oldest industries in the world. The multi-billion dollar industry ships tens of millions of units each year, with twin and queen size dimensions accounting for almost 60% of sales. In the past few decades innovations in mattress technology have focused on improving sleep quality, largely due to increased sleep science knowledge and new data revealing measureable consequences on brain health, cellular rejuvenation, metabolism, physical injury recovery, and stress relief. While mattress solutions have evolved, bedding material enhancements generally have not. Traditional bed sheets include a single top sheet and single bottom or fitted sheet layers beneath a blanket or cover, and there may be a mattress pad between the bottom sheet and the physical mattress. When people share the same bed for sleeping there may naturally be a difference in preferences for sleep conditions including environmental elements such as light level and temperature, fabric types, as well as material combinations, arrangements, configurations, and etc. Not surprisingly, two or more people sharing a single bed will have different routines and standards for achieving consistent quality in their respective sleep habits. And, regardless of the individual's age, physical or mental condition prior to entering a bed, it's reasonable to assume that maintaining preferred sleep conditions becomes elusive once an unconscious sleeper's involuntary behaviors ensue. Thus, sharing a bed can be undesirable because physical space and materials are also shared, and these situations can be unintentionally compromised or altered in manners that disturb and completely disrupt what otherwise would be a quality sleep experience.

SUMMARY

Bed sheets can be designed to accommodate individual sleep preferences for multiple people sharing the same bed. For example, compared to the personalized features of a sleeping bag such as interior space, material type, thread count and insulation it is possible to establish a bedding panel system where fastened materials and panel components are configured to create distinct physical sleep chamber spaces that provide multiple individuals customized sleep experiences in a single bed. Using a bedding panel system, where fasteners lock upper panels and cushions in place on top of a fitted or bottom sheet, enables any variety of materials and combinations of components to be installed beneath and above the individual in their respective sleep zone. This system establishes a customized environment that largely remains in place throughout the sleep period, providing added comfort and utility that ultimately improves sleep quality. A bedding panel system can be designed for any bed size where the number of sleep chamber spaces can range from two and up depending on the desired sleep zone sizes for a given mattress size. In some examples, a bedding panel system in king or queen size configurations may accommodate up to six or more individual sleep chambers, providing uniquely personalized utility and comfort in what otherwise would be a very unlikely setting for achieving qualitative sleep conditions for several people. And, similar to a sleeping bag, a bedding panel system with several individual sleep zones affords each sleeper elevated privacy levels and freedom from physical interaction with other sleepers, along with peace of mind that their preferred bedding material will not be displaced or accidently removed during sleep. A bedding panel system, with upper panels locked into the bottom or fitted sheet securing bedding materials surrounding each occupant, prevents alteration or accidental removal by unconscious or conscious activity from occupants sharing a bed. Multiple sleep chamber configurations for groups of individuals, e.g., children and smaller adults, enables a single bed to accommodate a variety of bedding material preferences simultaneously, e.g.—cotton or flannel, padded or unpadded, one layer or two, and etc. Similarly, head-to-toe sleep chamber configurations can be secured with anchors to provide even more autonomy and privacy for occupants in the same bed that prefer not sleep in the same direction.

BRIEF DESCRIPTION OF THE DRAWINGS

The present invention is illustrated by the accompanying drawings to provide examples of possible features, structures and operations for the disclosed subject matter, and not by way of limitation to any changes in form and detail that may be made by one skilled in the art within the spirit and scope of the disclosed implementations.

FIGS. 3C-F are illustrations of exemplary connection systems for bedding panel system components.

FIG. 8 is an illustration of rendered bedding panel system and related component data.

FIG. 9 is an illustration of rendered sleep analytic information and related user profile data.

DETAILED DESCRIPTION

The innovation describes a bedding panel system that allows two or more occupants to share a single bed in separate sleep chamber spaces comprised of various top panel modular configurations that are secured to a fitted sheet on the bottom. The bedding panel system can be modified using a combination of layered modular panels of particular sizes that are anchored to a fitted sheet, with utility and comfort features above and beneath each occupant that can be customized, according to the desired sleep experience preferences of the respective individuals. Physical sleep chamber spaces are established and thus create a "sleep zone" by fastening mechanisms that attach top modular panels to anchor channels embedded within a fitted sheet. A modular component system is possible where grid patterned anchor channel holes or ports sewn into fabric layers enable various panel sizes to be installed according to the desired sleeping space for each occupant. In some embodiments, anchor channels may be embedded within a fitted sheet such that an unlimited variety of modular panel combinations can be installed in different sizes, directions, positions, and layers.

Figure 1:
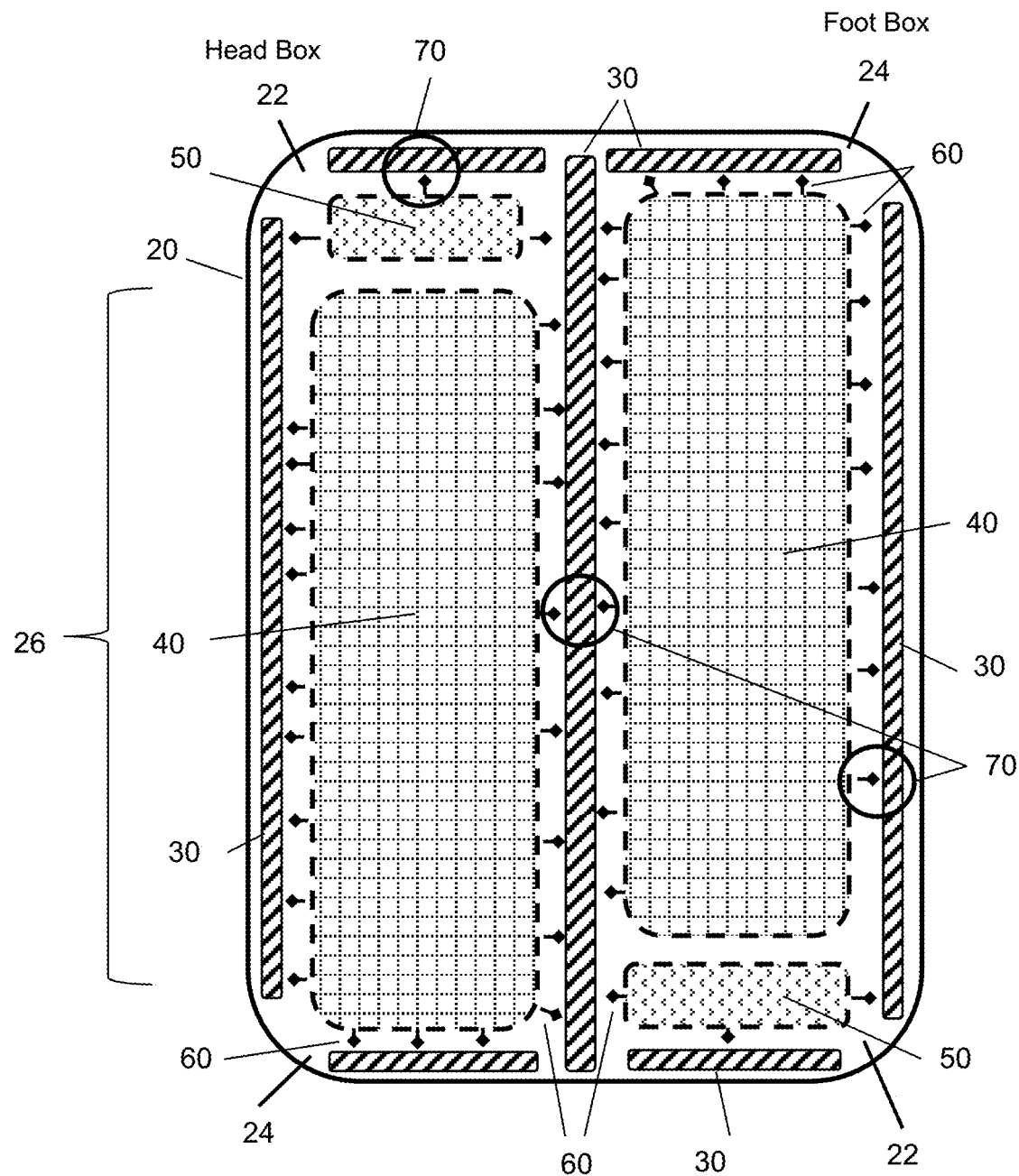
FIG. 1 is a top perspective view of an exemplary bedding panel system including fitted sheet, modular panels, cushion covers, channels and anchors.

Referring to FIG. 1, the present invention discloses a bedding panel system 10 is provided that is suitable for residential, commercial and recreational use. FIG. 1 shows a top perspective view of an exemplary bedding panel system 10. Bedding panel system 10 can include a fitted sheet 20 configured with a plurality of anchor channel 30, at least one modular panel 40 and at least one cushion cover 50. Modular panel 40 and cushion cover 50 may include one or more anchor 60. For reference, fitted sheet 20 may be referenced by head box 22, foot box 24 and interior 26 sections. In some embodiments, various types of connections may be made using a plurality of anchor channel 30 and anchor 60 comprised of hardware and material in various types, uniquely arranged, in combinations and specific implementations, hereinafter referred to as connection system 70, such that they may be utilized to connect modular panel 40 (hereinafter "panel or panels") and cushion cover 50 to fitted sheet 20 efficiently and effectively as detailed further in the disclosed innovations. FIG. 1 shows a configuration of an exemplary connection system 70 that enables two sleep zones to be established where head box 22 and foot box 24 are at opposite ends of a side-by-side configuration of bedding panel system 10. In the present example, two individual panel 40 from adjoined sleep chamber spaces are connected to the same anchor channel 30. In some embodiments, connection system 70 includes commonly known hardware, techniques and methods comprising anchor channel 30 and anchor 60 to secure panel and fitted sheet 20.

Figure 2A:
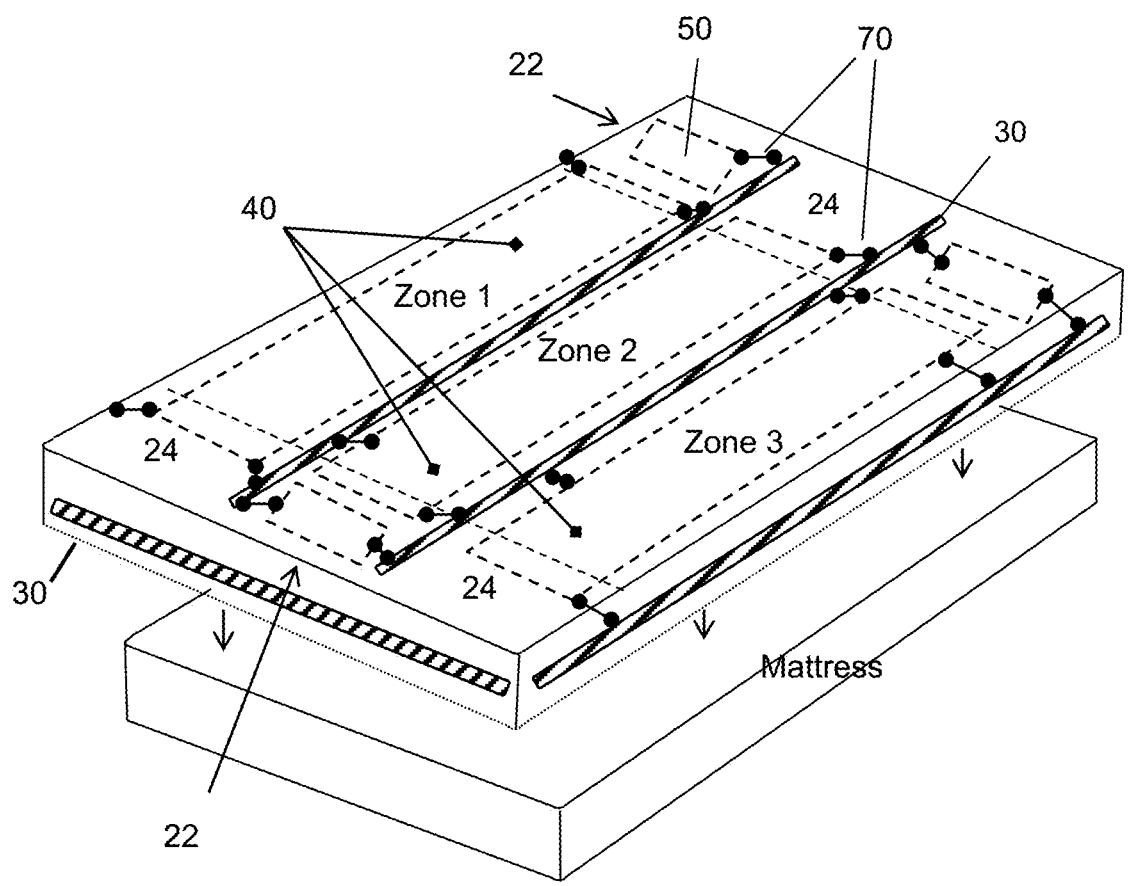
FIG. 2A is top view example of a bedding panel system in a three (3) zone configuration.
Figure 2B:
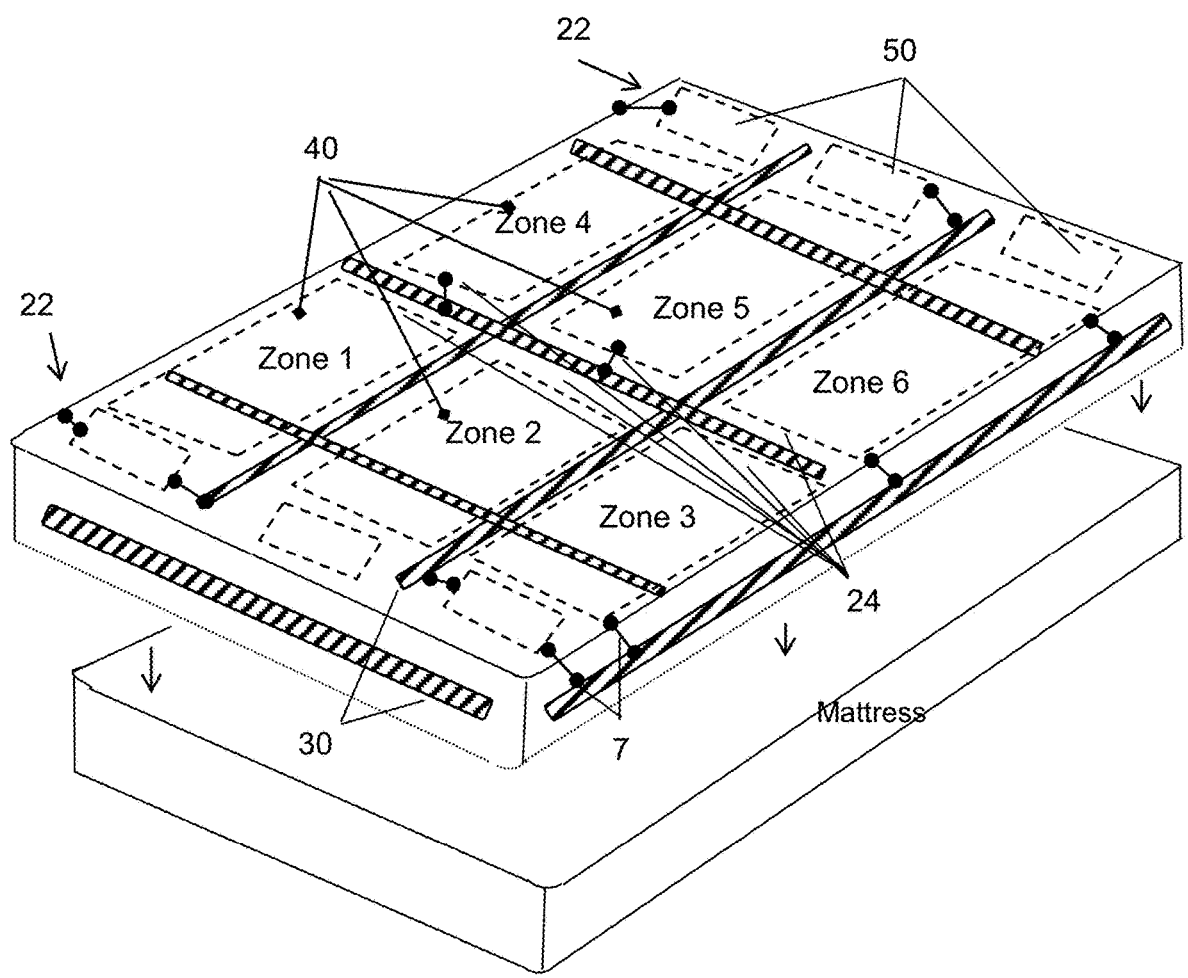
FIG. 2B is top view example of a bedding panel system in a six (6) zone configuration.
Figure 2C:
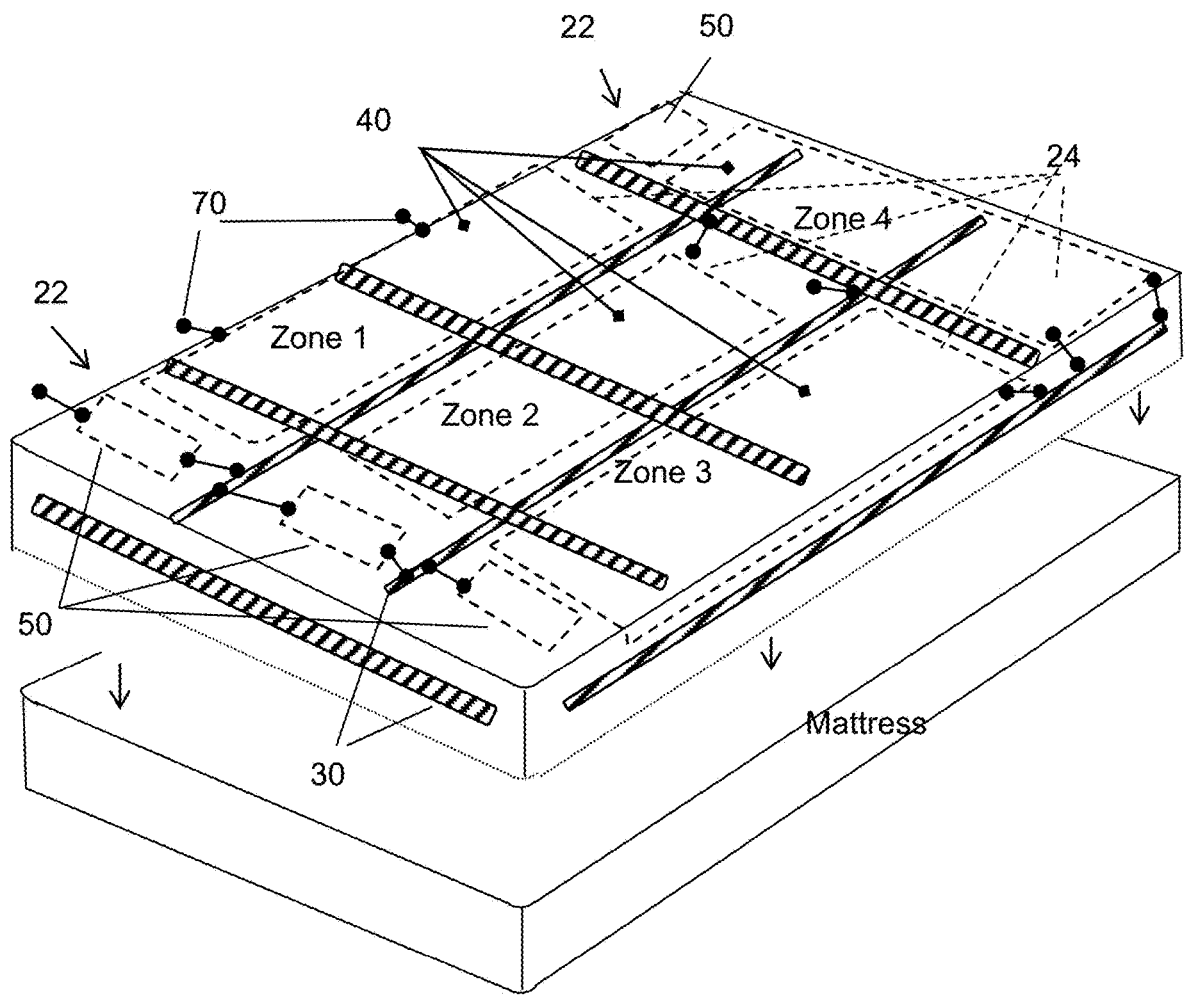
FIG. 2C is top view example of a bedding panel system in a four (4) zone configuration.

As presented in FIGS. 2A-C, exemplary illustrations depict variations of bedding panel system 10 embodiments that enable one or more panel 40 to be installed in different configurations on fitted sheet 20 such that users can create multiple independent sleep zones as well as position corresponding head box 22 and foot box 24 in different locations on the same bed. Panel 40 size dimensions are determined by the user's desired deployment in bedding panel system 10 for more than one individual, which provides potentially hundreds of panel combinations depending on the size of fitted sheet 20. In some embodiments, fitted sheet 20 may have features, dimensions and shape according to installation specifications on a comparably sized mattress including but not limited to crib, twin, twin XL, full, queen, king, Cal king or futon. In some other embodiments, fitted sheet 20 may be affixed to a mattress with anchoring materials such as elastic bands, hooks, snaps, string ties and the like to secure it to a mattress in a similar fashion as traditional fitted bed sheets. Depending on the bed occupant's desired sleep experience, panel 40 size and connection system 70 anchor count may vary based on the number of possible sleep zones that can be created in a given amount of space allotted on a mattress. For example, FIG. 2A illustrates a three-zone configuration 80 where multiples of modular panel 40 and cushion cover 50 can be installed in parallel using anchor channel 30 as well as at positions for head box 22 and foot box 24 at opposite ends to create greater separation between users. In some examples, as depicted in FIG. 2B, bedding panel system 10 in a six-zone configuration 84 establishes six separate zones for occupants where several head box 22 are arranged on both ends of fitted sheet 20, enabling six sleep chamber spaces to be created by multiple panel 40 and cushion cover 50 installed in anchor channel 30. In yet another example, FIG. 2C illustrates bedding panel system 10 in a four-zone configuration 88 where three head boxes are arranged on approximately two-thirds of fitted sheet 20 and a single zone is arranged perpendicularly to the others at one end of fitted sheet 20, with panel 40 and cushion cover 50 installed in anchor channel 30. Accordingly, as depicted by the above examples, when sized with the appropriate mattress, bedding panel system 10 may accommodate a large variety of sleep zone configurations using a connection system 70 and a plurality of different sized panel 40. And, for discussion purposes of the prescribed innovation, it is understood that the amount of available space in a sleep chamber is inverse to the number of desired sleep chambers. This consequence should be weighed against the health advantages, lifestyle convenience, privacy gains and utility features presented herein, especially for those individuals that may not have a choice of sleep space alternatives such as children that share beds to save space, or disabled and handicapped individuals needing assistance or safety measures during sleep periods.

Figure 3A:
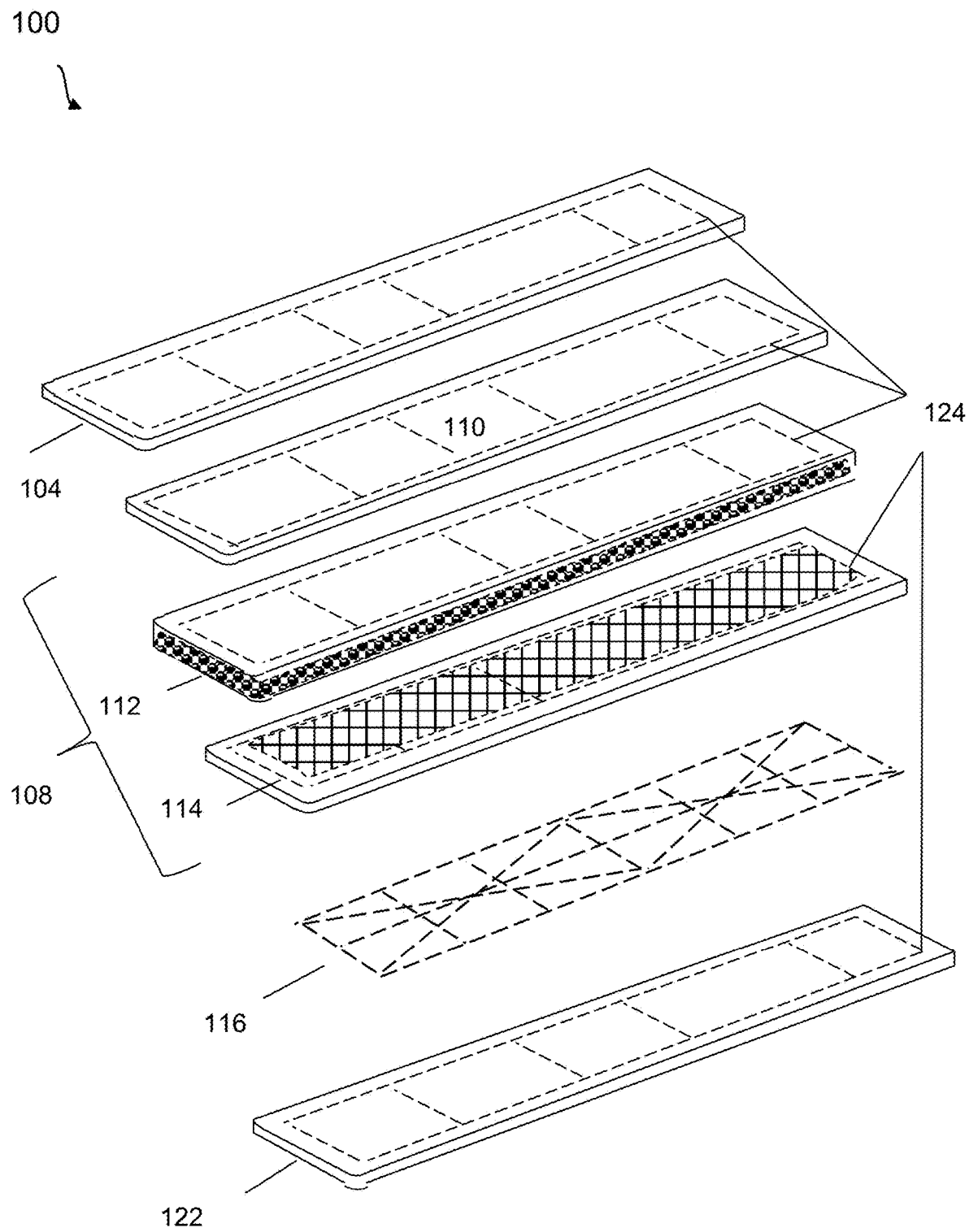
FIG. 3A is a sectional view of a bedding panel system fitted sheet.

FIG. 3A illustrates a detailed layered view of fitted sheet 100 structural components in accordance with the present disclosure. In some embodiments, fitted sheet 100 is fitted sheet 20. Fitted sheet 100 components are disclosed in detail herein for the purposes of presenting the utility and comfort advantages attained with bedding panel system 10 where the number of components, arrangements, configurations and the like are not limited solely to depictions and illustrations herein and may vary in volume, size, material composition, architecture and construction to achieve desired function and operation. For reference, fitted sheet 100 may be comprised of interchangeable components or layers. In some embodiments, fitted sheet 100 components include an upper lining 104, at least one inner lining 108, at least one anchor channel 116, and a lower lining 122. In some other embodiments, fitted sheet 100 components are sewn together into a single article that can be attached to a mattress of an appropriate size. In some further embodiments, fitted sheet 100 components are modular and can be added, connected, tied, aligned or subtracted, disconnected, untied, or detached from each other. In still further embodiments, anchor channel 116 is anchor channel 30.

Upper lining 104 is comprised of fabricated synthetic or textile material suitable for desired sleep comfort including but not limited to cotton varieties, silk, polyester, linen, flannel, wood pulp or material blend combinations manufactured with specific weave patterns and thread count specifications. In other embodiments, upper lining 104 is comprised of moisture repellant materials. In some other embodiments, upper lining 104 is comprised of moisture absorbing and moisture wicking materials. In some embodiments, inner lining 108 may encase one or more layered components with varying purpose and function, including but not limited to a water proof layer 110, cushion layer 112, and a technical layer 114. In other embodiments, multiple inner linings 108 can be installed between upper lining 104 and anchor channel 116. In some embodiments, water proof layer 110 is comprised of moisture repellant materials to provide a water proof barrier that protects cushion layer 112 and technical layer 114. In other embodiments, water proof layer 110 is comprised of moisture absorbing and moisture wicking materials to improve performance. In some other embodiments, water proof layer 110 is configured as a detachable upper lining 104. In some further embodiments, water proof layer 110 is inner lining 108.

Cushion layer 112 is comprised of materials for added padding, support, softness and comfort. In some embodiments, cushion layer 112 may be comprised of fabricated synthetic or textile material suitable for desired sleep comfort including but not limited to cotton varieties, wool, down, memory foam or material blend combinations. In other embodiments, cushion layer 112 architecture provides a barrier between fitted sheet 100 components designed for primary user contact, such as upper lining 104 and the more rigid and delicate components comprising technical layer 114 as well as durable and flexible materials of anchor channel 116, to better protect and preserve all elements of comprising fitted sheet 100 based on the rigors of typical user activity. Accordingly, cushion layer 112 architecture innovations anticipate atypical behaviors associated with the present invention such as above average user activity in defined physical spaces, greater than average weight in a single sleep environment, physical activity impact on connection system integrity, personal safety, and the like. In some further embodiments, there are multiple cushion layers 112 inside inner lining 108. Technical layer 114 includes controls, sensors and electronic components to manage sleep comfort such as monitoring and adjusting conditions based on biometric and environmental data each individual using bedding panel system 10 including but not limited to room temperature, body temperature, breathing, physical movement, audible sounds, object recognition, voice commands, and lighting levels as further detailed in FIGS. 5A-C.

In some embodiments, technical layer 114 is separate from cushion layer 112 such that technical layer 114 may be positioned above or beneath cushion layer 112 within inner lining 108. In other embodiments, there are technical layer 114 components embedded in cushion layer 112. In some further embodiments, technical layer 114 components are embedded throughout inner lining 108. In still further embodiments, technical layer 114 components are incorporated into material such that multiple sleep zones can be identified and independently managed on a single fitted sheet 20 within bedding panel system 10, such as low voltage RF sensors embedded in anchors 60 and anchor channel 116 that determine panel 40 size and orientation on fitted sheet 100. Anchor channel 116 may be embedded in each of fitted sheet 100 components, including upper lining 104, inner lining 108, water proof layer 110, cushion layer 112, technical layer 114, and lower lining 122. As detailed further in FIG. 3B, in some embodiments anchor channels 116 embedded in all fitted sheet 100 components may have reinforced holes 124 sewn or cut throughout anchor channel 116, corresponding to anchor channel 116 architecture which, depending on the sleep zone configuration described previously in FIGS. 2A-C, enables various customized connection system 70 applications between channel 30 and anchor 60. Lower lining 122 is comprised of materials for added padding, support, and durability of fitted sheet 100. In some embodiments, lower lining 122 is comprised of fabricated synthetic or textile material suitable for supporting and protecting fitted sheet 100 layers including but not limited to cotton varieties, synthetics, nylons or other material blend combinations.

Figure 3B:
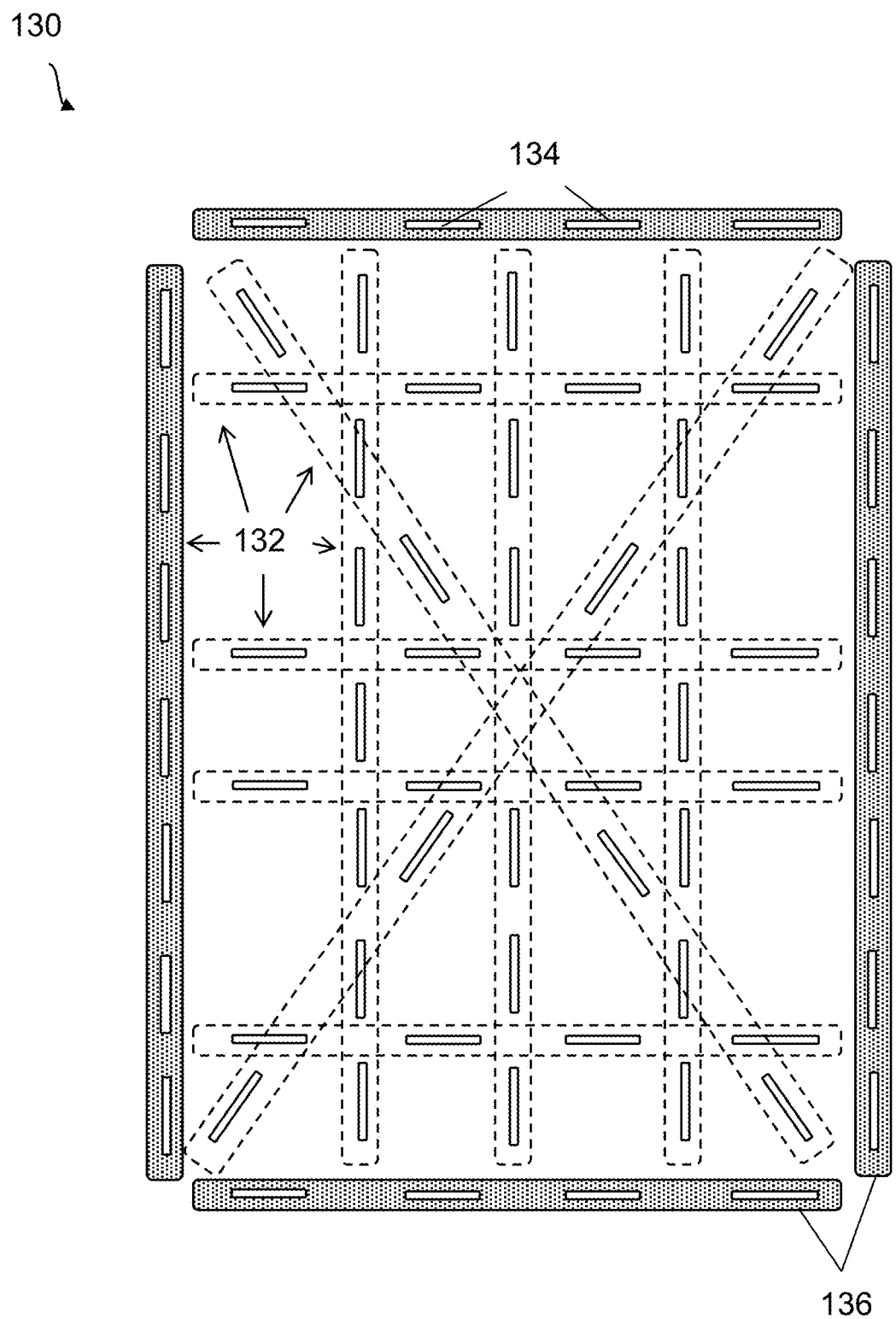
FIG. 3B is a detailed view of a fitted sheet anchor channel.

FIG. 3B shows a detailed view of an exemplary configuration of anchor channel 130. For discussion purposes, "anchor channel" may represent a single, group or plurality of anchor channels 130 in various arrangements, sizes and configurations deployed in bedding panel system 10. In some embodiments, anchor channel 130 is anchor channel 116. As described previously and in the representative drawing, anchor channel 130 may be deployed, arranged and embedded in each fitted sheet 100 layer or component layer in accordance with the desired sleep zone specification and mattress size. In some embodiments, anchor channel 130 is configured in a crisscross, diagonal, geometrical or pattern orientations throughout fitted sheet 100, creating numerous rows and columns to which multiple panel 40 and cushion 50 may be attached. In other embodiments, anchor channel 130 is comprised of durable and elastic materials 132 such as neoprene, rubber, polyester, latex, nylon, knits or spandex. Anchor channel 130 may be constructed with reinforced holes 134 in various sizes and patterns in accordance with a specific type of connection system 70 applications. In some embodiments, reinforced holes 134 on anchor channel 130 may be comprised of metal, plastic or fabric including but not limited to grommets, studs, eyelets and the like. In some embodiments, anchor channel 130 is embedded throughout fitted sheet 100 and respective component layers, including side panel anchor 136 located on all sides of bedding panel system 10 sized accordingly to the mattress it is installed on.

FIGS. 3C-F show several detailed views of exemplary connection system 140. In some embodiments, connection system 140 is connection system 70. In some embodiments, connection system 140 is comprised of at least one anchor channel 144, fastening material 146, anchor 148, and fastening method 150. In some embodiments, anchor channel 144 is anchor channel 130 and anchor channel 30. In some embodiments, anchor 148 is anchor 60. In other embodiments, connection system 140 may use a plurality of anchor channel 144, fastening material 146 and anchor 148 to secure panel 40 and cushion cover 50 to fitted sheet 100. In some other embodiments, connection system 140 comprises an arrangement of anchor channel 144 in a pattern aligned with reinforced hole 134 patterns of corresponding fitted sheet 100 components such that one or more modular panel 40 of different sizes may be efficiently and conveniently connected to a respective anchor channel 144 embedded in fitted sheet 100. In further embodiments, as referenced in FIG. 3B, anchor channel 130,144 is comprised of durable and elastic materials. Similarly, in some embodiments, fastening material 146 is also comprised of durable and elastic textile or synthetic material such as neoprene, rubber, polyester, latex, nylon, knits or spandex. In some other embodiments, fastening material 146 may be constructed in various length and width sizes in accordance with specific types of connection system 140 applications where system 10 component sizes and thickness determine the specification requirements. In some embodiments, at least one anchor 148 is affixed to fastening material 146. In other embodiments, anchor 148 may be comprised of plastic, rubber, metal, nylon, fabric or other materials created for hardware configurations including buttons, clasps, snaps, Velcro, zippers, buckles, toggle fasteners, hooks, pins, frog fastener, d-rings, magnets or similar fastening material.

Fastening method 150 defines a process for attaching and detaching bedding panel system 10 components. Generally, fastening method 150 describes the manner in which panel 40 and cushion cover 50 may be quickly and efficiently attached or detached from fitted sheet 100 by using selectively-operable methods or techniques according to a specific connection system 140 types and configuration. More specifically, based on the variations and combinations of possible fastening material 146 and anchor 148, fastening method 150 establishes a sequence, step, steps, action or actions applied by a user operating connection system 140 hardware and materials to secure and unsecure components to one another and allow safe, efficient and easy operation of the prescribed assembly.

As shown in FIG. 3C, in some embodiments, connection system 140 is demonstrated with a "single anchor" fastening method 150. In the present example, connection system 140 is comprised of a plurality of elongated pieces of fastening material 146 that are sewn into or affixed permanently to panel 40 and cushion cover 50 on one end in several locations, while the other ends are affixed to various types of anchors 148 that may be secured to anchor channel 144 embedded in fitted sheet 100. In the present example, panel 40 and cushion cover 50 may be attached or detached from fitted sheet 100 by a method 150 of inserting or removing anchors 148 from anchor channel 144 that are embedded in fitted sheet 100. As shown in FIG. 3D, in some embodiments, connection system 140 is demonstrated with a "double anchor" fastening method 150. In the present example, connection system 140 is comprised of a plurality of elongated rectangular strips or pieces of fastening material 146 affixed to anchor 148 on both ends that may secure panel 40 and cushion cover 50 with anchor channel 144 embedded in fitted sheet 100. In the present example, panel 40 and cushion cover 50 may be attached or detached by a method 150 of inserting or removing anchor 148 from anchor channel 144 that are embedded in fitted sheet 100, or inserting or removing anchor 148 from anchor channel 144 that is embedded in panel 40 and cushion cover 50. As shown in FIG. 3E, in some embodiments in some embodiments, connection system 140 is demonstrated with a "zipper" fastening method 150. In the present example, connection system 140 is comprised of is a zipper wherein one side of the zipper panel is sewn into or affixed to panel 40 and cushion cover 50 in several locations and the other side of the zipper panel is affixed to a plurality of elongated pieces of fastening material 146, each of which on the other end is affixed to anchor 148 that may be secured to anchor channel 144 embedded in fitted sheet 100. In the present example, panel 40 and cushion cover 50 may be attached or detached by a method 150 of zipping or unzipping a zipper that separates fastening material 146 from panel 40 and cushion cover 50.

As shown in FIG. 3F, in some embodiments, connection system 140 is demonstrated with a "double fastener" fastening method 150. In the present example, connection system 140 is comprised dual sets of fastening material 146 and anchor 148 which allow two connection systems 140 to be secured to anchor channel 144 embedded in fitted sheet 100. In the present example, two different panel 40 or cushion cover 50 may be attached or detached by a method 150 of inserting or removing anchor 148 from anchor channel 144 that are embedded in fitted sheet 100. To further the present example, where two panel 40 or cushion cover 50 may need securing at points where two adjoining sleep zones are created, the double fastener fastening method 150 will allow both panel 40 or cushion cover 50 to maintain a secure connection to the anchor channel 144. In some embodiments, this method may use anchor 148 types that are of flat and smooth, or shaped for interlocking connections, to avoid material bulk that impairs sleep comfort. It should be noted that connection system 140 functions and operations are not limited the depictions above and may facilitate secured connections of panel 40 or cushion cover 50 to anchor channel 144 using a variety of similar methods and techniques. Similarly, fastening material 146, anchor 148 and fastening method 150 may be embodied in different forms not detailed above that have the same function, shape or purpose of any of the aforementioned types in accordance with the functional, convenience and comfort goals of the innovations described herein.

Figure 4A:
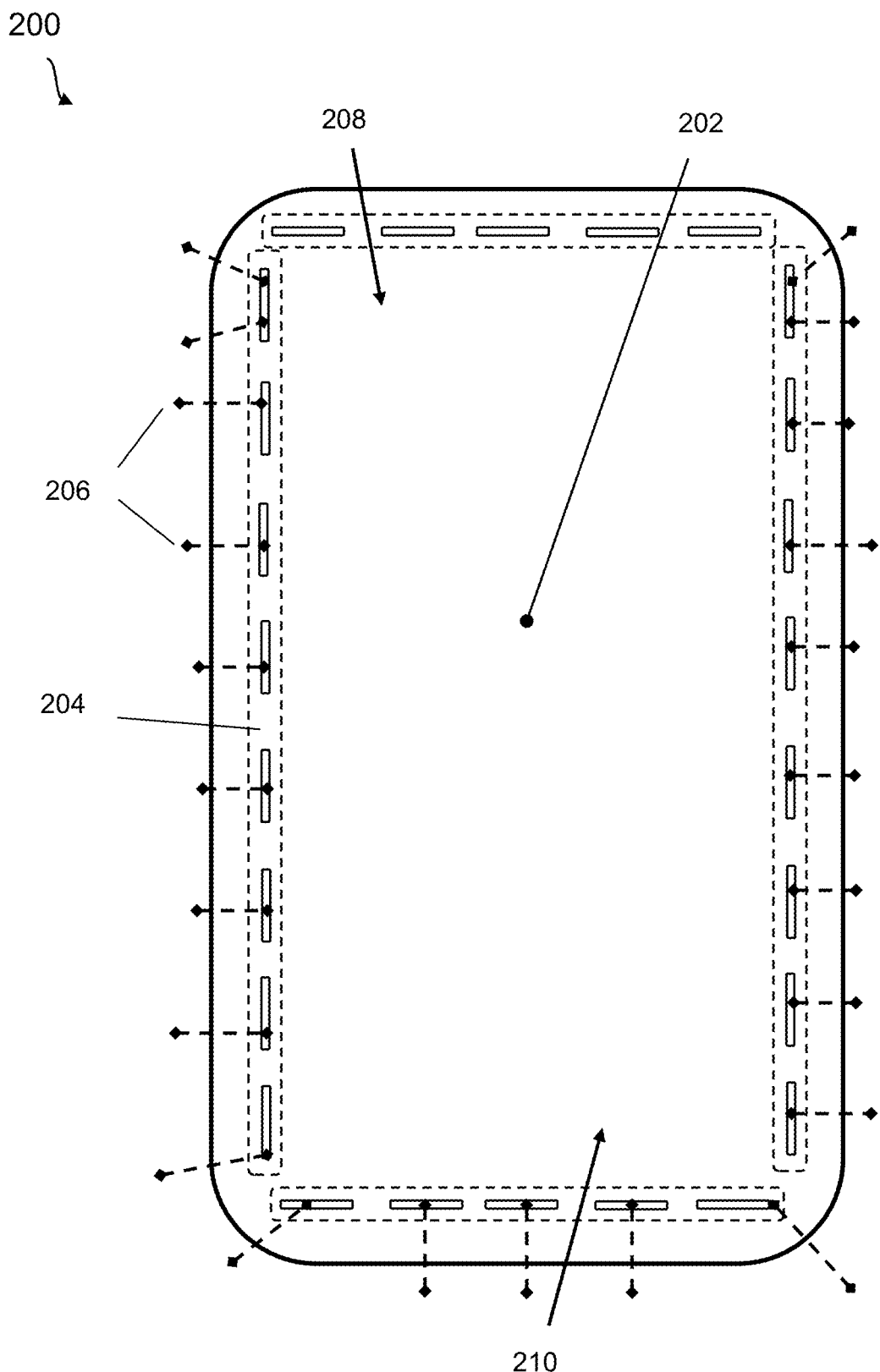
FIG. 4A is a top perspective view of a bedding panel system modular panel.

FIG. 4A illustrates an exemplary modular panel 200 in accordance with some embodiments of the present disclosure. In some embodiments, modular panel or panel 200 is panel 40. Overall, panel 200 components are disclosed in detail herein for the purposes of presenting the utility and comfort advantages attained with the present innovation where the number of components, arrangements, configurations and the like are not limited solely to depictions and illustrations herein and may vary in volume, size, material composition, architecture and construction to achieve desired function and operation. In some embodiments, panel 200 is comprised of at least one lining 202, at least one embedded anchor channel 204 and a plurality of connection system 206 such that panel 200 can be fastened to fitted sheet 100 in configurations that include different combinations of head box 208 and foot box 210 orientations in respective sleep zones. In other embodiments, panel 200 is comprised of multiple layers of lining 202, such as upper 222, inner 224-228, and lower 230 detailed in FIG. 4B. In some examples, anchor channel 204 is affixed to lining 202 via a technique or method such as sewing, gluing, fastening hardware and the like. In some embodiments, anchor channel 204 is anchor channel 116 and anchor channel 30. In some embodiments, connection system 206 is connection system 140 and connection system 70.

Figure 4B:
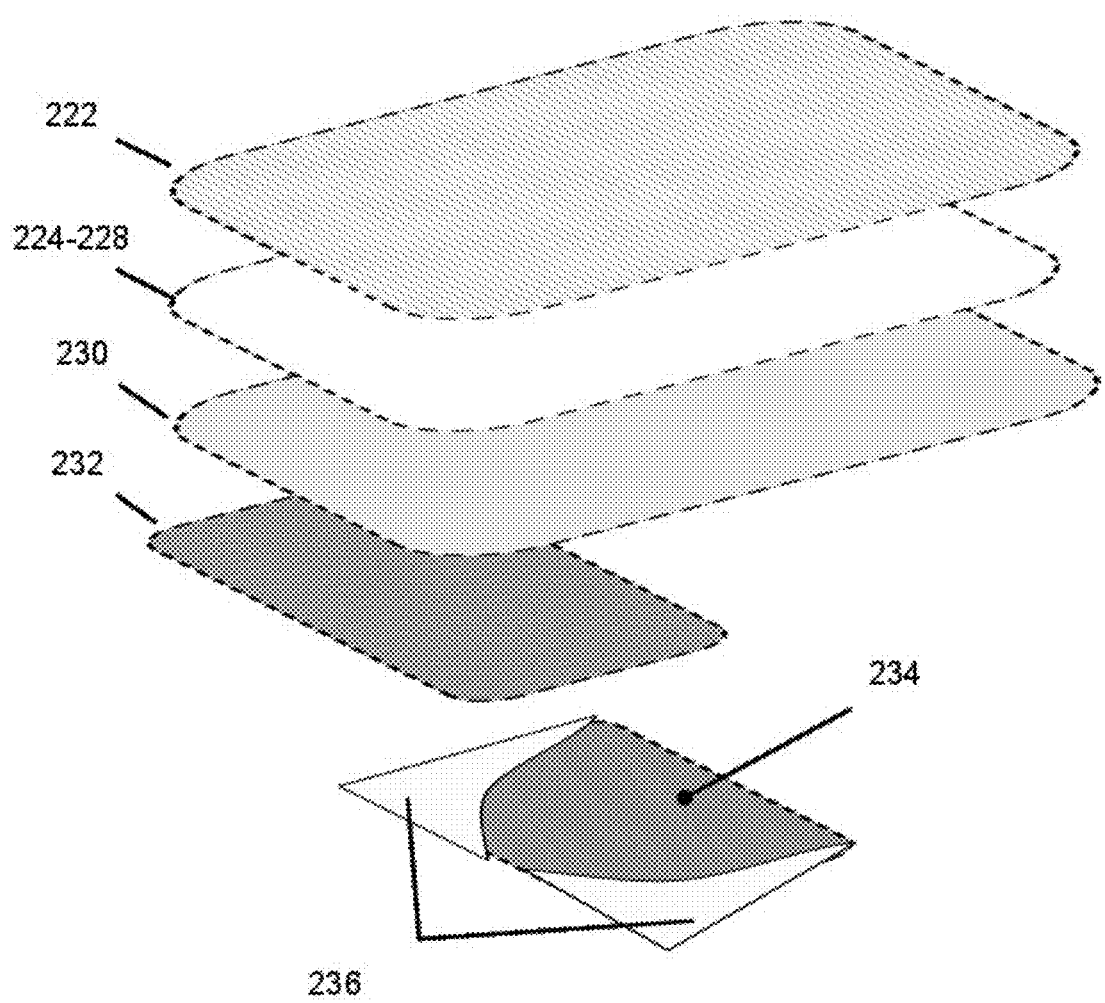
FIG. 4B is a sectional view of a bedding panel system modular panel.

As shown in FIG. 4B, similar to fitted sheet 100 architecture, a detailed view 220 of panel 200 may be comprised of interchangeable or layered components. In some embodiments, panel 200 may have varying size dimensions depending on the desired sleep zone installations, including but not limited to those depicted in FIG. 2A-C. In some embodiments, panel 200 includes an upper lining 222, at least one or more inner linings 224-228, lower lining 230 and foot panel 232. In another embodiment, panel 200 components are sewn together into a single article that can be attached to a mattress of an appropriate size. In some other embodiments, panel 200 components are modular and can be added, connected, tied, aligned or subtracted, disconnected, untied, or detached from each other and independently attached to fitted sheet 100 architecture. In some further embodiments, upper lining 222 is lining 202. In still further embodiments, upper lining 222 is comprised of fabricated synthetic or textile material suitable for desired sleep comfort including but not limited to cotton varieties, silk, polyester, linen, flannel, wood pulp or material blend combinations manufactured with specific weave patterns and thread count specifications.

One or more inner linings 224-228 may comprise panel 200 components with varying purpose and function. In one embodiment, inner lining 224 is comprised of insulation and padding material for comfort and warmth such as cotton, wool, foam or other synthetic blends. In another embodiment, inner lining 224 is comprised of fabric encased glass beads that add weight to panel 200 for greater sleep comfort. In one embodiment, inner lining 226 is comprised of moisture repellant materials to provide a water proof barrier that protects panel 200 components from absorbing moisture and water. In another embodiment, inner lining 226 has absorbing and moisture wicking materials to retain moisture and draw water away from a subject while sleeping. In one embodiment, inner lining 228 is comprised of electronic sensors and actuators that measure sleep related conditions and data to enable automated control of bedding panel system 10 components that manage sleep quality. In another embodiment, inner lining 228 is technical layer 114. Lower lining 230 is comprised of fabricated synthetic or textile material suitable for desired sleep comfort including but not limited to cotton varieties, silk, polyester, linen, flannel, wood pulp or material blend combinations manufactured with specific weave patterns and thread count specifications.

Foot panel 232 is comprised of material designed for foot and lower leg comfort including but not limited to cotton varieties, silk, polyester, linen, flannel, wood pulp or material blend combinations manufactured with specific weave patterns and thread count specifications. In some embodiments, foot panel 232 is technical layer 114. In some examples, foot panel 232 is shaped and sized to be installed in the foot box 210 portion of a particular sleep zone such that it has direct contact with a user's feet. In another embodiment, foot panel 232 is comprised of material containing deodorizing or an odor absorbing material such as charcoal, baking soda, baby powder, corn starch, and talcum powder and the like. In other embodiments, foot panel 232 is comprised of material encased in fabric such as glass beads, contoured foam, rubber balls and similar techniques that massage the subject's feet during sleep. In some other embodiments, foot panel 232 may be comprised of materials implemented as motion-restraints 234 to retard or lessen physical motion in the foot box 210 portion of a particular sleep zone. In some embodiments, motion-restraints 234 may be comprised of flexible, stretchable, pliable or elastic materials arranged to minimize the force generated by lower leg movement from an occupant in a particular sleep zone to reduce disruption of sleep quality for other sleep zone occupants. In other embodiments, motion-restraints 234 involve material that is patterned 236 to accommodate an occupant's sleep comfort and create a functional space for force limiting functions, such as v-shaped, cone-shaped or tube-shaped configuration. In some examples, motion-restraint 234 material comprised of fiber or synthetic materials such as polyester, lycra, latex, nylon, knits, neoprene or spandex.

Figure 4C:
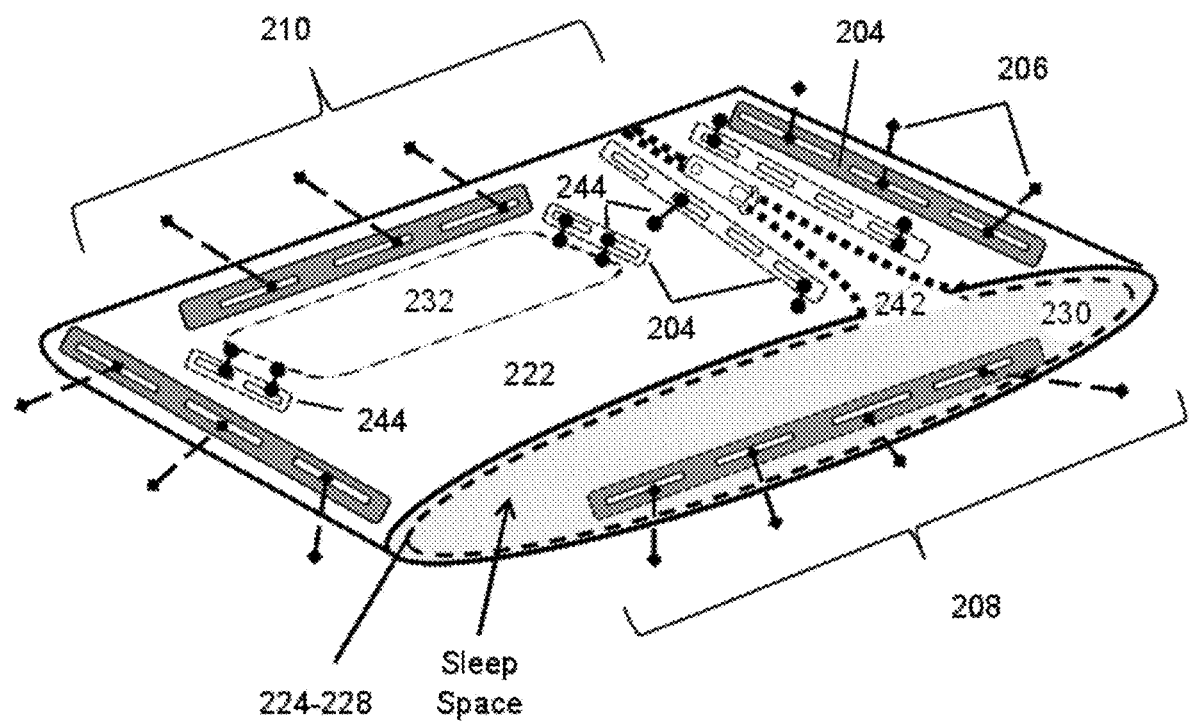
FIG. 4C is a drawing of a bedding panel system sleep sack.

FIG. 4C illustrates an exemplary sleep sack panel 240 in accordance with some embodiments of the present disclosure. Overall, sleep sack panel 240 components are disclosed in detail herein for the purposes of presenting the utility and comfort advantages attained with the present innovation where the number of components, arrangements, configurations and the like are not limited solely to depictions and illustrations herein and may vary in volume, size, material composition, architecture and construction to achieve desired function and operation. Sleep sack panel 240 is comprised of at least one embedded anchor channel 204, a plurality of connection system 206, upper lining 222 on the outside of the apparatus, at least one or more inner linings 224-228, lower lining 230 on the inside of the apparatus, a foot panel 232, a quick access mechanism 242, and a plurality of sleep sack anchor 244. In some embodiments, sleep sack panel 240 is constructed in a sack or bag type configuration where foot box 210 area and the majority of material surrounding the sleep chamber are permanently closed or sealed and head box 208 is open for user ingress and egress, creating a sleep chamber space similar to that afforded by a traditional sleeping bag. In one embodiment, at least one embedded anchor channel 204 and a plurality of connection system 206 enable sleep sack panel 240 to be fastened to fitted sheet 100.

In some embodiments, sleep sack panel 240 may have a quick access mechanism 242 affixed to one or more portions of the apparatus to enable easy and efficient ingress and egress for users from inside or outside the apparatus. In some embodiments, quick access mechanism 242 is connection system 140 configured according to fastening method 150 as depicted in FIGS. 3C-F. Quick access mechanism 242 may be comprised of plastic, rubber, metal, nylon, fabric or other materials created for hardware configurations including buttons, clasps, snaps, Velcro, zippers, magnets or similar fastening materials. In one example, quick access mechanism 242 is a zipper installed on upper lining 222 traveling the length of sleep sack panel 240 starting at head box 208 to approximately the beginning of foot box 210. In another example, quick access mechanism 242 is a Velcro strip installed on upper lining 222 traveling the length of sleep sack panel 240 starting at head box 208 to approximately the beginning of foot box 210. In still another example, quick access mechanism 242 is a row of button snaps installed on upper lining 222 traveling the length of sleep sack panel 240 starting at head box 208 to approximately the beginning of foot box 210. In yet another example, quick access mechanism 242 is a row of magnets installed on upper lining 222 traveling the length of sleep sack panel 240 starting at head box 208 to approximately the beginning of foot box 210. Sleep sack anchor 244 may be comprised of plastic, rubber, metal, nylon, fabric or other materials created for hardware configurations including buttons, clasps, snaps, Velcro, zippers, magnets or similar fastening materials. In one embodiment, sleep sack anchor 244 enable sleep sack panel 240 to secure foot panel 232 to anchor channel 204. In some embodiments, anchor channel 204 is positioned within sleep sack panel 240 components to secure them to one another using sleep sack anchor 244 in a manner that enables quick access mechanism 242 function using selectively-operable methods or techniques according to a specific quick access mechanism 242 type and configuration. In the present example, sections of upper lining 222 may connect to one or more inner linings 224-228 and lower lining 232 using sleep sack anchor 244.

In some embodiments, sleep sack panel 240 may function as a standalone portable apparatus to be used in different lifestyle settings. In one example, sleep sack panel 240 may be installed in chair designed for mobile or mass transit travelers such as car, airplane, bus, or boat or train where connection system 206 may be fastened to existing apparatus. In some other examples, sleep sack 240 may be offered for use at commercial and private host sleep spaces such as hotels, motels, hostels, rental homes, AirBnB's or cabins where fitted sheets 100 onsite are made available onsite. In still other examples, the bed occupier may travel with sleep sack 240 from one host location to another, where the respective host provides details of available fitted sheet 100 configurations according to available bed sizes. In further examples, sleep sack 240 may be moved from a first bedding panel system 10 to a second bedding panel system 10 where, via internet or smart phone connections, a user's sleep preferences can be transferred from a cloud storage or smartphone memory to the second bedding panel system 10 in accordance with stored data associated with a user account, as described in FIGS. 7-9.

Figure 5A:
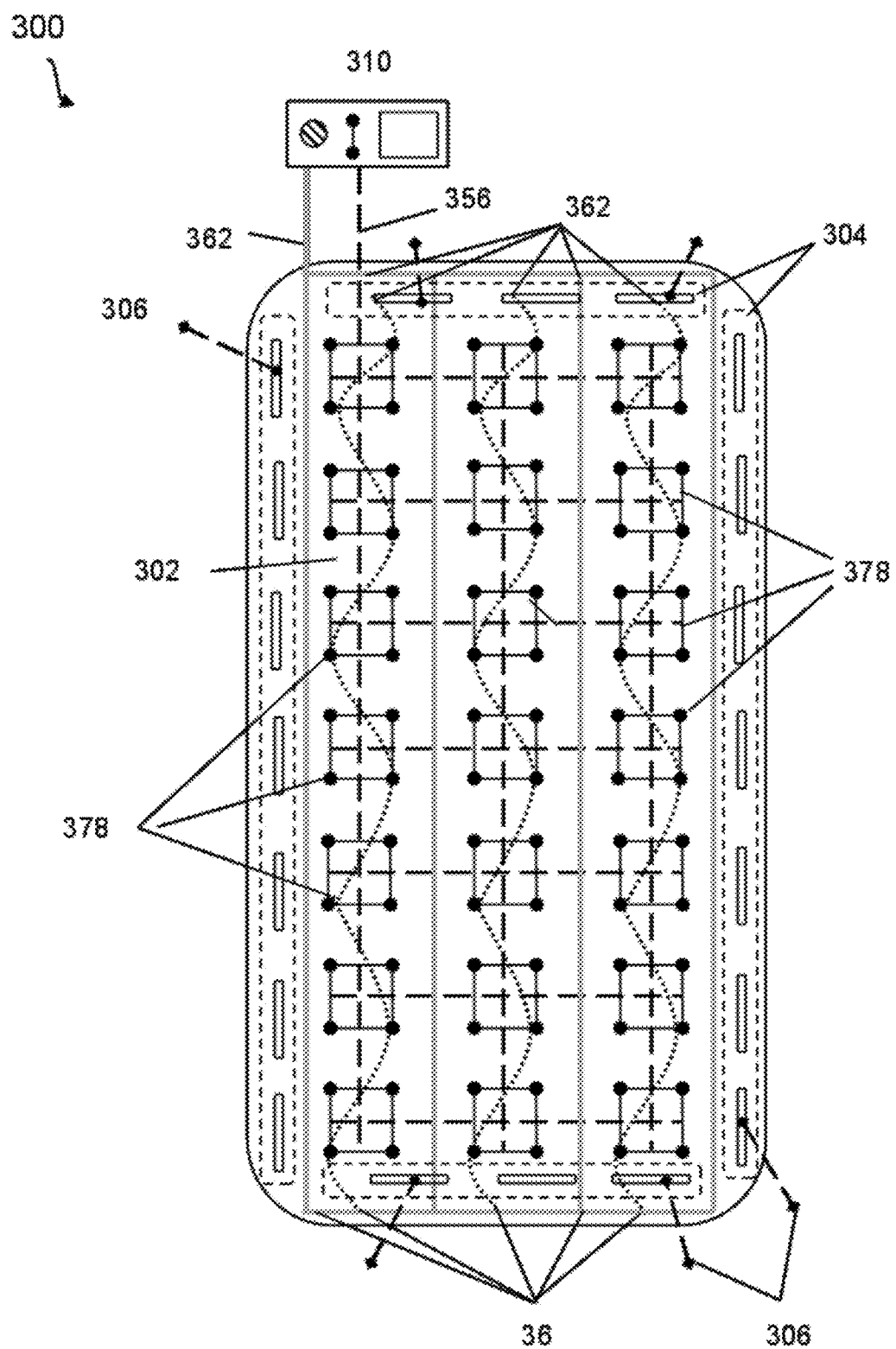
FIG. 5A is detailed view of a bedding panel system technical layer.

FIG. 5A illustrates an exemplary technical layer 300. Technical layer 300 is comprised of at least one lining 302, at least on anchor channel 304, a plurality of connection system 306, control unit 310, wire network 356, comfort system 362, and sleep monitor system 378. In some embodiments, technical layer 300 is technical layer 114. In some embodiments, technical layer 300 is inner lining 218. In some embodiments, lining 302 is upper lining 212 and lower lining 222. In some embodiments, anchor channel 304 is anchor channel 204. In some embodiments, connection system 306 is connection system 140. Generally, technical layer 300 may function such that direct user inputs (haptic controls or voice commands) from a control unit, wireless controls via smartphone app, or passive sensor capture methods are used to identify sleep pattern and sleep space condition data that can be interpreted to deliver optimal sleeping results. In some embodiments, lining 302 function and architecture is similar to inner lining 108 and includes multiple layers of material that encase, cover and protect technical layer 300 components. In some embodiments, technical layer 300 is inner lining 108.

Figure 5B:
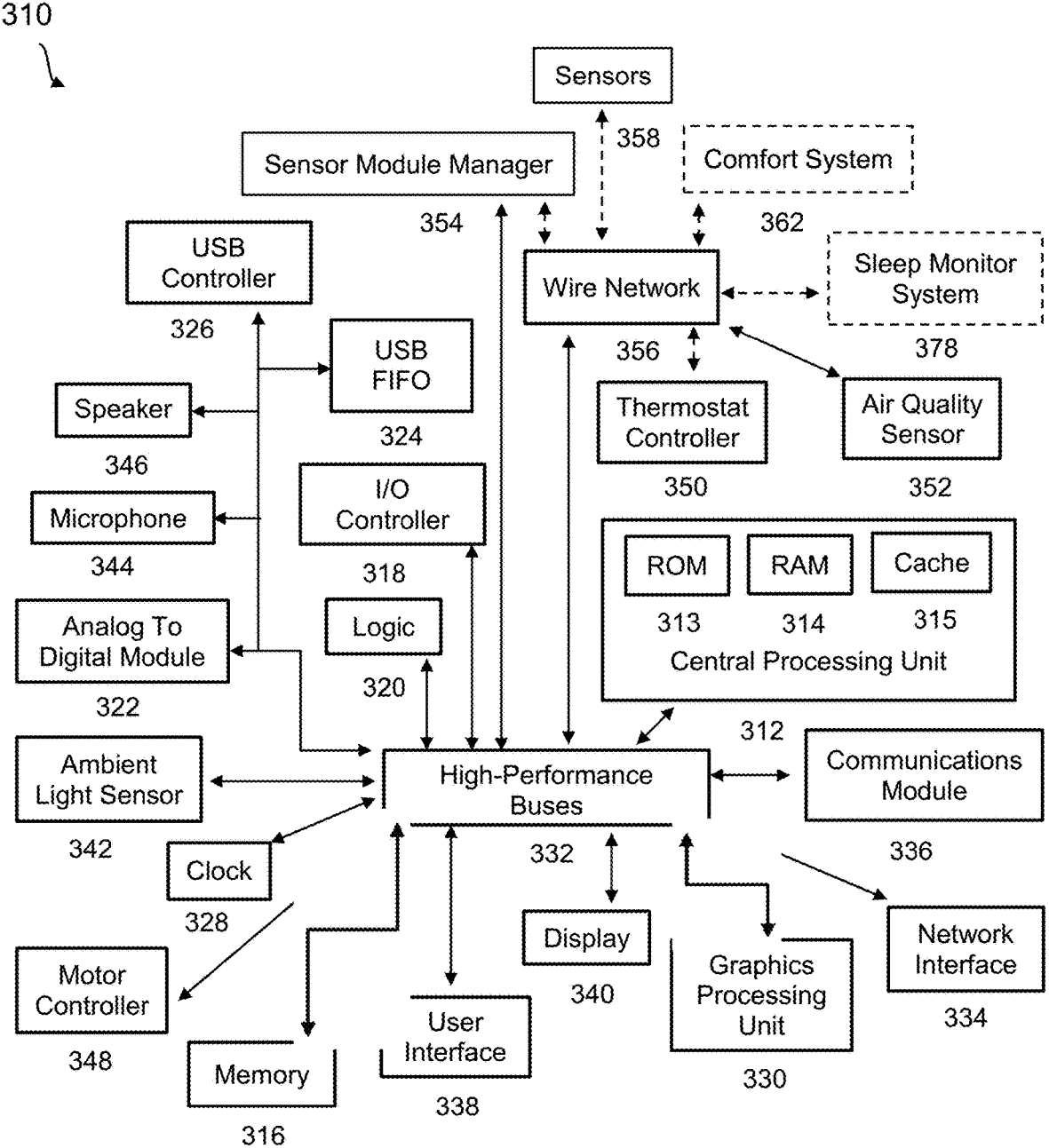
FIG. 5B is diagram of a technical layer control unit.

FIG. 5B shows a detailed view of control unit 310. In some embodiments, control unit 310 operates technical layer 300 components, including wire network 356, comfort system 362 and sleep monitor system 378 with manual controls, electronic controls, computer operating software, and automated computerized controls. In some embodiments, control unit 310 components include central processing unit (CPU or processor) 312, Read Only Memory (ROM) 313, Random Access Memory (RAM) 314 and at least one cache 315 to temporarily store data and improve processing efficiency. Processor 312 may utilize a non-volatile or volatile flash memory 316 for temporary data storage. Control unit 310 may include I/O controller 318, logic module 320, analog to digital module 322, USB FIFO unit 324, USB controller 326, clock 328, graphic processing unit 330, buses 332, network interface 334, and communications module 336. CPU 312 and various other components of control unit 310 are interconnected via one or more buses 332, including serial and parallel buses, a memory bus, a peripheral bus, and a processor or local bus using a variety of bus architectures. I/O controller 318 may manage data input and output to and from control unit 310. Logic module 320 may manage automated functions of control unit 310. Analog to digital module 322 may convert analog signals into digital data. USB FIFO unit 324 acts as a buffer between various components that supply data to USB controller 326 that operates to manage data flow. Clock 328 may be used to determine the schedule for automated functions on control unit 310 and associated components and external devices. Network interface 334 may manage connections between control unit 310 and communications between system components, connected smart devices, a database, the internet, or remote cloud database containing user account data.

Communications module 336 may operate to enable wired or wireless access to other devices and/or a network (e.g. private network, wide area network, ISP, local network, internet) and may be any of a variety of various wired or wireless components including Bluetooth, BLE, IR, optical, WiMax, RFID, Wi-Fi and the like. Control unit 310 may include a user interface 338, display 340, ambient light sensor 342, microphone 344, and speakers 346. User interface 338 may be used to manually operate control unit 310 and technical layer 300 components. In some examples, control unit 310 may be operated using haptic physical controls, such as a touch pad or alphanumeric keys, or voice commands configured via software application configured with microphone 344 and speaker 344. In some other examples, user interface 338 may be connected to and remotely operated by a networked mobile device application using firmware and communications module 336. Display 340 may display graphics, images, pictures, alphanumeric characters, and the like. Ambient light sensor 342 may be used detect changes in light intensity. Microphone 344 may be used to capture audio including audible speech, voice activated speech, voice commands, and ambient sounds. Speakers 346 may be used to broadcast audio sent to control unit 310 and communications module 336. Control unit 310 may include a motor controller 348, thermostat controller 350, air quality sensor 352, sensor module manager 354 and sensors 358. Motor controller 348 may be used to operate and send commands via wire network 356 to motorized, mechanical and electronic components of comfort system 362 and sleep monitor system 378. Thermostat controller 350 may be used to operate and send commands temperature via wire network 356 to related components of comfort system 362 and sleep monitor system 378. Air quality sensor 352 may be used to detect and send air quality data via wire network 356 to related components of comfort system 362 and sleep monitor system 378. In some embodiments, sensor module manager 354 may be used to communicate sensor 358 data, controls functions and commands between components of wire network 356, comfort system 362, sleep monitor system 378 and control unit 310. Sensors 358 may include monitoring, detecting, measuring apparatus that is distributed, embedded, affixed or arranged in, throughout or about technical layer 300 in such a manner to achieve optimal performance and communication accuracy of comfort system 362 and sleep monitor system 378, as detailed further in FIG. 5C. In some embodiments, sensor module manager 354 may be used to communicate sensor 358 data, controls functions and commands for wire network 356, comfort system 362, sleep monitor system 378 and control unit 310 to local and remote peripherals, connected smart devices, databases, cloud storage, networked components, and the like.

In some embodiments, using hardware and software applications, control unit 310 can associate a physical or geographical space located on specific fitted sheet 100 or "sleep zone" with a specific panel 200 to establish, monitor and record data from a unique physical sleep chamber space within bedding panel system 10. In other embodiments, control unit 310 can associate multiple fitted sheet 100 sleep zones with specific panels 200 to establish multiple unique physical sleep chamber spaces within bedding panel system 10, each with customized materials, components and technical settings. In some embodiments, RF sensors 358 embedded in connection system 206 identify location and orientation of fitted sheet 100 and one or more panel 200, providing a map of prospective sleep zones according to the desired range of possible configurations of connection system 206. In other examples, sleep zones may be defined by an occupant performing a sleep zone assignment operation using control unit 10 components including, but not limited to, sensor module manager 354, comfort system 362 and sleep monitor system 378. In some other embodiments, using real-time and/or stored sensor 358 data, control unit 310 can assign an occupant's sleep preference data settings to a specific sleep chamber space in bedding panel system 10, where preset settings may determine operations and performance of wire network 356, comfort system 362, and sleep monitor system 378 components for a specific sleep zone. In further embodiments, control unit 310 can assign occupant sleep preference data settings for to multiple physical sleep chamber spaces in bedding panel system 10 that determine operations and performance of wire network 356, comfort system 362, and sleep monitor system 378 components for all sleep zones identified in bedding panel system 10. In still further embodiments, once fitted sheet 100 and panel 200 are within a proximate range of each other in a sleep space within bedding panel system 10, control unit 310 can automatically detect an assigned sleep zone in fitted sheet 100 associated with a specific panel 200 using the wire network 362 and sensors 358 embedded in the respective components.

Figure 5C:
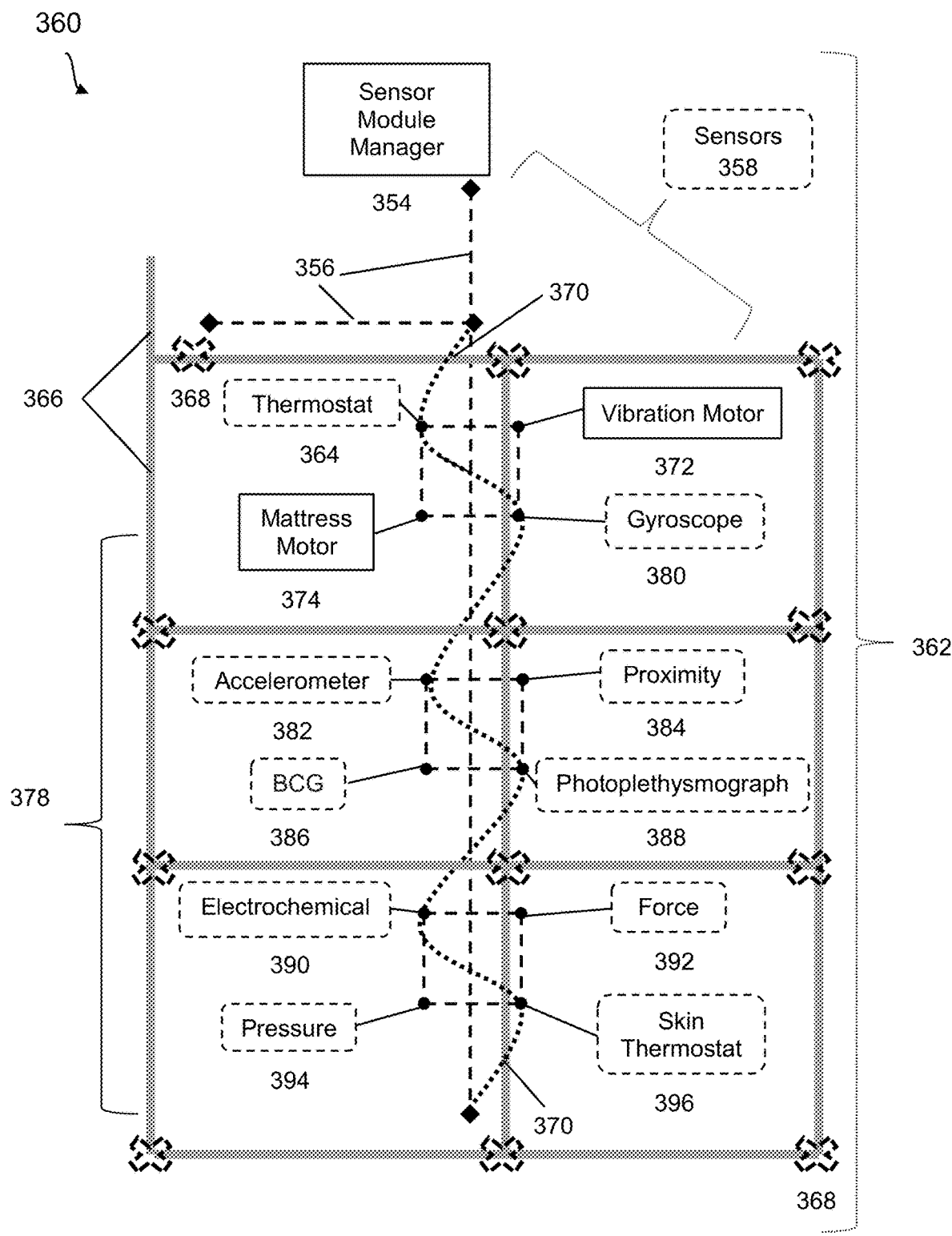
FIG. 5C is a detailed view of a wiring network, comfort system and sleep monitor system.

FIG. 5C shows a detailed view 360 of technical layer 300 components including wire network 356, comfort system 362 and sleep monitor system 378. Generally, wire network 356 is comprised of power and communications hardware with wiring connection architecture that allows control unit 310 to send and receive data from sensors 358 and related components, deliver function commands, retrieve sensor 358 measurement data, monitor technical layer 300 components, and the like. In the present example, the detailed view 360 of technical layer 300 components is not limiting and in some embodiments there may be a plurality of respective components and devices deployed to achieve the prescribed operation or technical functions. In one embodiment, sensor module manager 354 manages power, operation and data communications between control unit 310 and wire network 356, comfort system 362, sleep monitor system 378 and sensors 358. In some embodiments, wire network 356 enables control unit 310 to independently operate individual devices and components that comprise comfort system 362 and sleep monitor system 378. In other embodiments, wire network 356 enables control unit 310 to operate individual devices and components that comprise comfort system 362 and sleep monitor system 378 in conjunction with one another. In some other embodiments, sensor module manager 354 and wire network 356 enable control unit 310 to operate individual devices and components that comprise comfort system 362 and sleep monitor system 378 using automated computer programs and user profile data in accordance with stored activity data historically, available sleep environment condition data, or preset operational settings defined by the user. In the present example, control unit 310 may function to create different technical layer 300 component settings in separate sleep zones for either or both comfort system 362 and sleep monitor system 378 according to fitted sheet 100 and panel 200 sleep zone configurations depicted in FIGS. 2A-C.

In some embodiments, comfort system 362 is comprised of thermostat 364, venting tube 366, fan 368, heating element 370, vibration motor 372 and mattress motor 374. In some embodiments, comfort system 362 is comprised of a plurality of component types as part of the technical layer 300 architecture deployed in multiple sleep zones including at least one of the following: thermostat 364, venting tube 366, fan 368, heating element 370, vibration motor 372 and mattress motor 374. Thermostat 364 may be used to monitor component and zone temperatures throughout technical layer 300. In some embodiments, thermostat 364 is sensor 358. Heating element 370 may be used to increase temperature in a sleep chamber space between fitted sheet 100 and panel 200. In some embodiments, a plurality of heat elements 370 may be deployed to respective sleep zones as shown in FIGS. 2A-C. Venting tube 366 may be used with at least one fan 368 to draw air from within or blow air into fitted sheet 100 and panel 200 to reduce temperature inside a sleep chamber space between fitted sheet 100 and panel 200. In some examples, a plurality of venting tubes 366 may be deployed to respective sleep zones as shown in FIGS. 2A-C.

In some embodiments, thermostat 364 and control unit 310 may operate in conjunction to regulate heating and cooling functions with components such as fan 368 and venting tube 366 or heating element 370 to maintain a consistent temperature within a specific sleep zone during an occupants sleep period. In some embodiments, control unit 310 may raise or lower temperatures in respective sleep zones according to which sensors 358 are assigned to each panel 200 and fitted sheet 100 orientation, where detected sleep zones have technical configuration within bedding panel system 10 that defines head box 22, foot box 24 and interior 26 sections. In some examples, thermostat 364 and control unit 310 may operate technical layer 300 components to maintain different temperatures in multiple sleep zones during simultaneous sleep periods for multiple occupants. Vibration motor 372 may be used to generate pulsating and vibrating sensations within fitted sheet 100 and panel 200. Mattress motor 374 may be used to operate mechanical mattress controls to change the position or configuration of a mattress that fitted sheet 100 is affixed to.

In some embodiments, sleep monitor system 378 is comprised of a plurality of sensors 358 that detect physical and physiological data from individual sleepers in respective fitted sheet 100 and panel 200 sleep chamber spaces. In some embodiments, sensors 358 are connected to control unit 310 via wired or wireless communication signals. Sensors 358 sensors may be distributed, embedded, affixed or arranged in, throughout or about technical layer 300 in such a manner to achieve optimal performance and accuracy. In some embodiments, sleep monitor system 378 uses different types of sensors 358 for detecting, measuring and monitoring including but not limited to piezoelectric sensors, piezo resistive sensors, passive sensors with wireless read-out electronics, resistivity-based sensing devices, conductive threads, embedded smart material, flexible sensors, flexible electronic skin technologies, and the like. In some embodiments, sleep monitor system 378 is comprised of a plurality of sensor 358 component types as part of the technical layer 300 architecture in multiple sleep zones including but not limited to at least one of the following: multi-axis gyroscope 380, accelerometer 382, proximity sensor 384, ballistocardiograph (BCG) sensor 386, photoplethysmographic sensor 388, electrochemical sensor 390, force sensor 392, pressure sensor 394, and skin thermostat 396. In some embodiments, multi-axis gyroscope 380 may collect physical data indicating horizontal and vertical movement, angular movement. Accelerometer sensor 382 may be used to record the rate of movement activity and specific movement patterns. Proximity sensor 384 may be used to detect, movement, individuals and objects within a specific physical range of the sensor. Ballistocardiograph (BCG) sensor 386 may be used measure of ballistic forces generated by the heart. Photoplethysmographic sensor 388 may be used to monitor heart rate, blood pressure and oxygen levels. Electrochemical sensor 390 may be used to measure body fluids such as sweat, tears, and pH levels. Force sensor 392 may be a force transducer or strain gauge that converts a force such as tension, compression, pressure, or torque into an electrical signal that can be measured and standardized to measure weight. Pressure sensor 394 may be used to detect torsion, bending, or vibrations. Digital temperature thermostat sensor 396 may be used to detect skin temperatures. In some embodiments, sleep monitor system 378 may detect and measure physiological signals that represent heart rate data including but not limited to heart rate variability, the amplitude stroke volume, stroke volume variability, respiration rate respiration rate, and respiration rate variability. In other embodiments, sleep monitor system 378 may detect and measure physiological data signals that represent sleep data metrics including but not limited to sleep cycles, sleep stage, breathing patterns, irregular breathing patterns, breathing frequency, number of awakenings during the night, stress and the like. In still other embodiments, sleep monitor system 378 communicates with control unit 310 to transmit and receive sensor 358 and related component related commands. In further embodiments, sleep monitor system 378 communicates with control unit 310 via network interface 334 and communications module 336 to transmit and receive sensor 358, technical layer 300 component and user activity data to and from user data accounts, connected smart devices, cloud storage database, remote monitoring devices, and the like.

Figure 6:
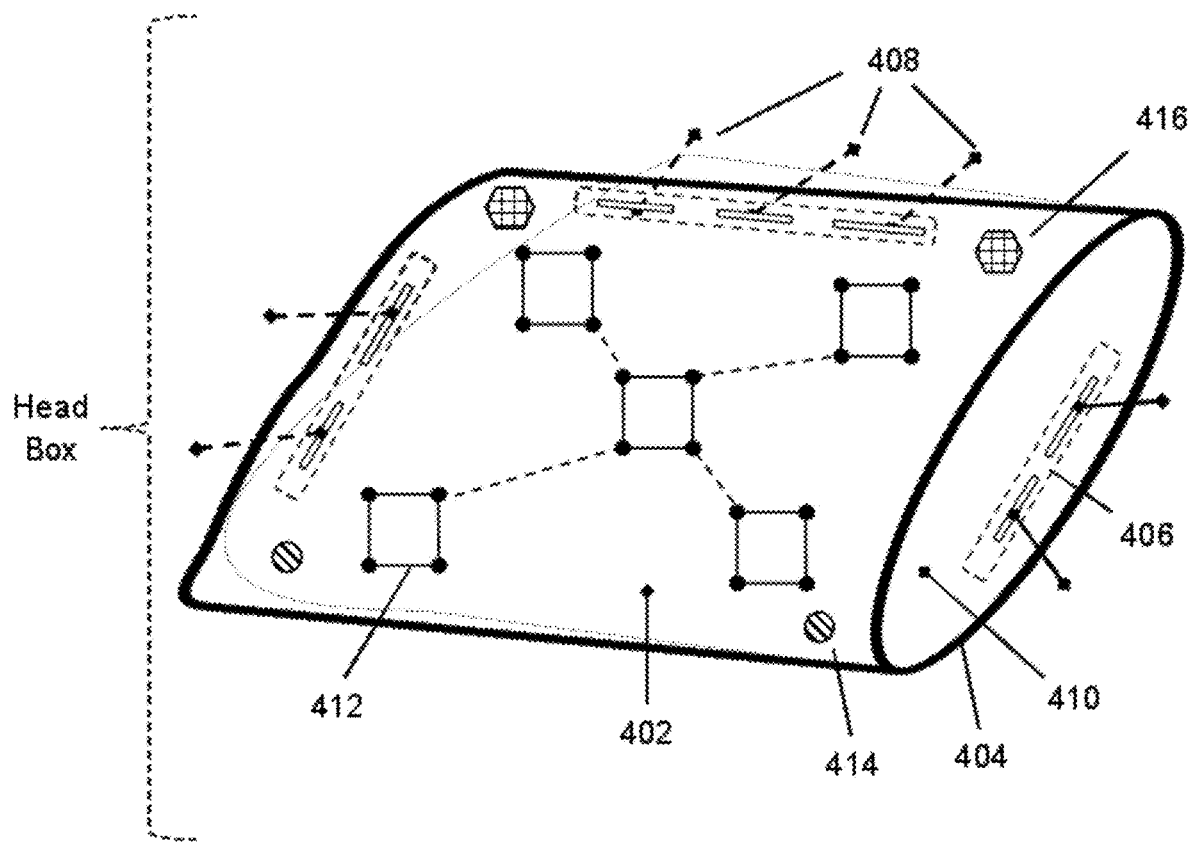
FIG. 6 is an illustration of bedding panel system cushion cover.

FIG. 6 illustrates an exemplary cushion cover 400. In some embodiments, cushion cover 400 is cushion cover 50. Generally, in some embodiments, cushion cover 400 physical attributes and dimensions may be similar to bed cushion covers or pillow cases of various sizes. In other embodiments, cushion cover 400 is a small-sized version of sleep sack 240 designed for use in fitted sheet 100 head box 208 area. In some embodiments, cushion cover 400 is comprised of an upper lining 402, at least one or more inner linings 404, at least one embedded anchor channel 406, a plurality of connection systems 408, lower lining 410, head monitor system 412, microphone 414, and speakers 416. In some embodiments, upper lining 402 is lining 212. In other embodiments, upper lining 402 is comprised of fabricated synthetic or textile material suitable for desired sleep comfort including but not limited to cotton varieties, wool, down, memory foam or material blend combinations. In some embodiments, inner lining 404 is at least one or more of inner linings 214-218. Inner lining 404, in one embodiment, may be comprised of moisture or liquid repellant material. Inner lining 404, in another embodiment, is inner lining 214 comprised of insulation and padding material for comfort such as cotton, wool, foam or other synthetic blends. In some embodiments, anchor channel 406 is anchor channel 204.

In some embodiments, connection system 408 is connection system 206. In some embodiments, lower lining 410 is lower lining 220. In other embodiments, lower lining 410 is comprised of moisture or liquid repellant material. In some embodiments, head monitor system 412 is sleep monitor system 378. In the present example, head monitor system 412 may be embedded in inner lining 404. In the present example, head monitor system 412 may be connected to audio and voice capture microphones 414 and audible sound broadcast speakers 416 embedded in inner lining 404. In some examples, head monitor system 412 is connected to microphone 414 and speakers 416 via wired or wireless means. In some embodiments, head monitor system 412 operates in conjunction with sleep monitor system 378 where user data collected from respective sleep zones is correlated with data collected from a corresponding cushion cover 400. In some embodiments, head monitor system 412 communicates with control unit 310 to transmit sensor 358 data, receive sensor 358 and device related commands, monitor sensor 358 and devices, and receive control unit 310 commands.

Figure 7:
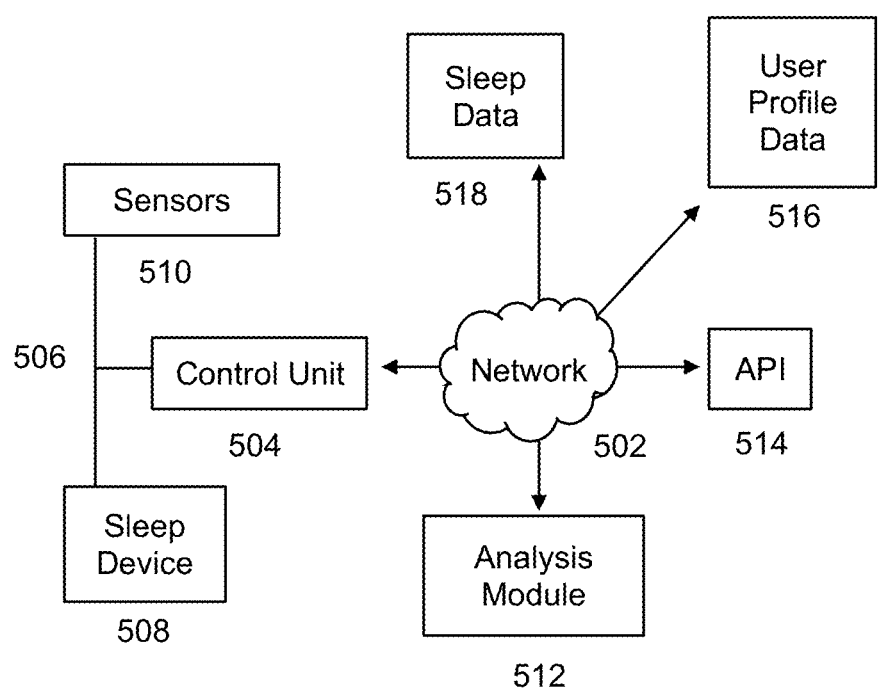
FIG. 7 is a diagram of a sleep analytics system.

FIG. 7 shows an exemplary sleep analytics system 500 for managing sleep data and related hardware component information. Generally, sleep analytics system 500 enables computerized software programming for capturing, indexing, storing, processing, analysis and sharing of sleep related information originating from bedding panel system 10 components and related user activity. In some embodiments, sleep analytics system 500 components may include a network 502, control unit 504, component network 506, one or more sleep device 508, one or more sensor 510, analysis module 512, an application program interface 514, user profile data 516, and sleep data record 518. In one embodiment, sleep analytics system 500 correlates and analyzes acquired sleep related information with user profile data 516 to identify and create sleep data record 518 including, but not limited to, sleep behavior, habits, preferences and quality metrics for each user of the system 500 during their sleep periods. In some instances, sleep data record 518 may be based on unique conditions established by bedding panel system 10 and related components during sleep periods including hardware settings, sleep zone settings, physiological data, behavioral data, environmental conditions, user control of hardware components, and the like. In some embodiments, control unit 504 is control unit 310. In some embodiments, component network 506 is wire network 356. In some embodiments, sleep device 508 is comfort system 362. In other embodiments, sleep device 508 is sleep monitor system 378. In some embodiments, sensor 510 is sensor 358. In some embodiments, sleep analytics system 500 operates software programming including an analysis module 512 for processing and analyzing user data, component data, and sleep related information originating from bedding panel system 10 components and related user activity.

In some embodiments, sleep analytics system 500 facilitates user profile data 516 and sleep data record 518 communications via application program interface (API) 514. In some examples, API 514 enables user profile data 516 and sleep data record 518 information to be transmitted and received between bedding panel system 10 components and local on-site users, remote users, servers and cloud data storage and servers. In some embodiments, control unit 504 may be equipped with wired or wireless communication means for import or export of user profile 516 and sleep data record 518 to and from a portable computing device or networked computing peripheral. In some embodiments, control unit 504 is equipped with a network 502 communications module via component network 506, such as communication module 336, for connecting to the internet, remote database, local network server, smart devices and the like. In other embodiments, control unit 504 communicates via network 502 with an application program interface or API 514 connected to a cloud based server or database configured to manage computerized programs for managing user activity data and analyzing sleep analytics data and related bedding panel system 10 information. In some embodiments, API 514 provides users access via locally connected or remote networked multimedia peripheral device to bedding panel system 10 information such as control unit 504 programming, sleep device 508 data, sensor 510 data, analysis module 512 data, as well as user profile 516 and sleep data record 518. In some embodiments, API 514 enables operation of control unit 504, sleep devices 508, and sensors 510 with user controls on a local or remotely networked multimedia peripheral device.

In some embodiments, API 514 software programming includes access to analysis module 512. In some embodiments, API 514 may be used to access and control analysis module 512 processes, information acquired from sleep devices 508 and sensors 510 as well as captured and stored user profile data 516 and sleep data record 518. In some embodiments, analysis module 512 operates processing and analytic programs on control unit 504. In another embodiment, analysis module 512 operates processing and analytic programs on a cloud database server. In some embodiments, analysis module 512 operates software programs for comparative, predictive, and recommendation analytic applications as detailed further in FIG. 9.

In one example, analysis module 512 processes data to measure sleep experience and related factors, as depicted in FIGS. 8-9, referenced to as sleep experience information. Sleep experience information may be comprised of objective and subjective information available for a user interacting with bedding panel system 10 including, but not limited to, data acquired via user surveys, direct user input of sleep quality preference data, sleep science research data, almanac information, weather information, medical science research data, as well as real-time and historical measurable data from the described innovations. In some embodiments, analysis module 512 acquires sleep experience reference data, from the internet or cloud server database via network 502 using automated computer search programs, for analysis, comparison, prediction and recommendation software applications and programs operated via API 514, control unit 504 and related bedding panel system 10 components. In another example, analysis module 512 processes data to score or rank sleep experiences and related sleep quality factors in a range of metrics including, but not limited to, a numerical rating, sleep environment rating, REM level experience, deep sleep levels, healthy biometric levels, and the like. In yet another example, analysis module 512 processes render data in a variety of formats such as statistics, charts, graphs, imagery and other visualizations to communicate sleep data information to users and appropriate audiences. In still yet another example, analysis module 512 processes data to make recommendations for bedding panel system 10 configurations, conditions and settings that are customized based on available sleep experience information, user profile 516 information, historical sleep data record 518 analytics by individuals, and aggregated sleep data record 518 analytics from generic or anonymized user groups. In some embodiments, represented in FIGS. 8-9, informational formats associated with sleep data record 518 may be displayed on a networked multimedia peripheral device operating API 514 including data associated with bedding panel system 10 components and configurations, alphanumerical values, charts, calendars, histograms, sensor values, device setting values, physiological information, behavioral information, activity level measurements, audio files, sleep quality factors list, notification lists, recommendation lists and the like.

In some embodiments, analysis module 512 may obtain, index, process, store and monitor data from devices and embedded technologies in bedding panel system 10 components including, but not limited to, fitted sheet 100, panel 200, sleep sack 240, control unit 310 and cushion cover 400. In some other embodiments, analysis module 512 uses machine learning programming to identify, index, measure, and process sleep experience information, sleep data record 518 categories, values, patterns, trends and the like. In further embodiments, analysis module 512 uses artificial intelligence algorithm calculations of user profile 516 and sleep data record 518 to determine accurate sleep data record 518 categories, values, patterns, trends and the like. In still further embodiments, analysis module 512 uses computer programs including but not limited to algorithmic and machine learning calculations of sleep experience information, user profile 516 and sleep data record 518 to determine opportunities or conditions for quality sleep and make recommendations for optimal outcomes accordingly. In yet still other embodiments, analysis module 512 is configured to process available objective sleep data record 518 metrics including, but not limited to, available sleep experience information air quality, room temperature, physical location, weather, seasonal factors, and the like. In yet further embodiments, analysis module 512 is configured to process subjective sleep data record 518 metrics including, but not limited to, sleep and wake times, sleep stage duration, physical movements, audible distractions, biometrics, bed partners, and the like that may identified as factors or influencers of sleep quality for a user. In still yet another embodiment, analysis module 512 is configured to interpret objective and subjective sleep experience information and sleep data record 518 categories, values and related metrics unique to each user of the system and designated sleep zone.

In one example, analysis module 512 is configured to identify, measure and monitor sleep cycles and sleep stages associated with a user. In the present example, analysis module 512 may identify the number of sleep cycles for light sleep and a deep sleep, time for each cycle, phases of REM sleep, duration of REM sleep phases, and related sleep stage information. In the present example, analysis module 512 may obtain reference data via network 502 from a database, internet sources, or unique demographic group for sleep data comparative analytics, sleep quality factor analysis, formulating recommendations for improving sleep quality. In the present example, analysis module 512 may compile sleep data record 518 based on a single sleep related event, over cumulative sleep sessions and, with machine learning or artificial intelligence programming, determine data integrity, reliability and accuracy of analyzed information according to the totality of available information processed. Still in the present example, analysis module 512 may process sleep experience information, user data 516 and sleep data record 518 to determine a user's sleep related behaviors and lifestyle including but not limited to sleep routine, sleep patterns, impairments to sleep quality, factors that promote sleep quality, and the like. In another example, analysis module 512 may process sensor 510 data to identify biometric data, including but not limited to heart rate, pulse rate, blood pressure for users of each respective sleep zone configured on fitted sheet 100. In yet another example, analysis module 512 may identify proximity and pressure data to determine the physical position, ingress and egress patterns for users of each respective sleep zone configured on fitted sheet 100 and panel 200. In the present example, pressure 394 and proximity 384 sensors placed on head box sections of fitted sheet 100 and panel 200, as well as sleep sack 240 and cushion cover 400, may indicate separation of material components that identifies ingress and egress movement activity. In still yet another example, where sensor 510 is embodied as an RF, Bluetooth or similar detection device, control unit 504 and analysis module 512 may identify proximity and activity data of detached or portable personal objects associated with users of each respective sleep zone configured on fitted sheet 100, such as smart phones, smart watches, smart TV, smart speakers and the like. In a further example, using pressure 394 sensors, analysis module 512 may measure the physical weight associated with users of each respective sleep zone configured on fitted sheet 100. In still a further example, analysis module 512 processing and analysis of cushion cover 400 and related sensor 510 data may identify sleep disorders or irregularities such as snoring, sleep apnea, respiratory stress, and the like. In yet another example, analysis module 512 processing and analysis of cushion cover 400 and related sensor 510 data may identify voices, audible sounds, and noises associated with users of each respective sleep zone configured on fitted sheet 100 and panel 200. In still another example, analysis module 512 may identify and measure the movements and physical activity level associated with users of each respective sleep zone configured on fitted sheet 100 and panel 200. In still a further example, analysis module 512 may identify and measure stress, discomfort, disturbed sleep, and physical pain associated with users of each respective sleep zone configured on fitted sheet 100. In yet still a further example, analysis module 512 may identify and measure moisture levels in fitted sheet 100, panel 200, sleep sack 240 and cushion cover 400 to determine levels moisture present in each respective sleep zone. For each of the aforementioned examples above, including sleep data record 518 metrics not referenced but measurable by sleep analytics system 500, analysis module 512 may be configured to establish a data sequence threshold, limit, numerical value or combination thereof that triggers a data recording of the event or experience, store collected information on user profile 516 records, and deliver an alert notification of the data record to a networked multimedia peripheral device operating API 514.

In another embodiment, sleep analytics system 500 may process and monitor user profile 516 and sleep data record 518 based on data benchmarks, thresholds, anomalies, events, or cumulative events such that the system generates a data record, notation, alert or notification to a networked multimedia peripheral device via network 502 and API 514. In one example, an alert or notification may be sent to API 514 operated by a caregiver if sleep analytics system 500 were to detect a sleep zone in which the user exhibited sleep related anomalies or health status concerns such as an above average heart rate, abnormal body temperature, elevated physical activity, and the like. In another example, sleep analytics system 500 may send ongoing user profile 516 and sleep data record 518 to a remotely located caregiver, from the beginning to the end of a user's sleep routine, via a data stream delivered from network 502 and API 514. For the examples provided above, sleep analytics system 500 may store the user profile data 516 preferences in control unit 310, memory 316 or on a cloud storage database via the network interface 336 for API access, general reference, and updates by the system and users therein.

In some embodiments, API 514 can associate a specific fitted sheet 100 sleep zone with a panel 200, including related control unit 504, sleep device 508 and sensor 510 applications. In another embodiment, API 514 can be operated to assign user profile information to a specific fitted sheet 100 sleep zone and associated panel 200, including related control unit 504, device 508 and sensor 510 applications. In another embodiment, via control unit 504, API 514 can operate to automatically detect and assign a sleep zone in fitted sheet 100 to a specific panel 200 using component network 506 and sensors 510 embedded in the respective components. In some embodiments, sleep analytics system 500 may enable bedding panel system 10 components via network 502 to operate devices equipped with internet of things (IoT) protocols on a local network. In one example, sleep analytics system 500 may operate an alarm device, lights or lighting controls, pneumatic or adjustable bed controls, an audio broadcast device, a computer, a television, a coffee maker and etc. In another example, control unit 504 may capture biometric data indicating that a user has entered into a specific sleep stage benchmark or threshold, based on API 514 and control unit 504 settings, which in turn may initiate IoT commands. In the present example, IoT commands may include directions for controls that change lighting setting, television operations, audible books, sound or music broadcasts as well as connected appliances. In a further example, IoT commands may be programmed with API 514 and control unit 504 settings to synchronize operations with bedding panel system 10 components as sleep aids such as vibrating motor 372, thermostat 364, heating element 370, fan 368, or speakers 346, 416. In still another example, control unit 504 may capture sleep data record 518 for use by the analysis module 512 in real-time to change or adjust sensors 510 and devices 508 to settings that can positively impact sleep outcomes during sleep periods, based algorithmic programming, such as bedding material temperature, vibrations, mattress position, audible sounds, room lighting and etc. In a further example, user profile 516 and sleep data record 518 may be used by the analysis module 512 to prepare optimal sleep conditions before the sleep period begins, during the sleep period, and ending sleep stages based on historical data and machine learning programs that use predictive analytics of user preferences that may control bedding material temperature, audio, lighting, alarms and the like.

FIG. 8 depicts bedding panel system 10 component data 530 generated by sleep analytics system 500. In some embodiments, component data 530 is displayed on a local or remote networked multimedia peripheral device using API 514. In other embodiments, component data 530 is displayed on control unit 504. In some other embodiments, component data 530 presents a profile summary 532 of one or more bedding panel system 10 installations including associated hardware components, software settings and related configurations. In the present example, installation for "Bed #1" and "Bed #2" includes, but is not limited to, descriptions of sleep zone configurations, connected sensors, connected comfort systems, connected devices, connected panels and sacks, available user profile data 516. In further embodiments, component data 530 presents user profile data 516 and sleep data record 518. In the present example, user profile data 516 may include, but is not limited to, user name, associated sleep zone, associated bedding panel system 10 components, user sleep preference data and available sleep experience information. Still in the present example, sleep data record 518 may include, but is not limited to sleep experience information, sleep quality metrics, sleep metrics ratings data, measured data accuracy rating, available sleep history data, analysis of sleep quality factors and influencers. In some embodiments, control unit 504 operates sleep device 508 and sensor 510 settings according to user interaction with bedding panel system 10 components. In some examples, user interactions may include operating physical controls of control unit 504, voice commands received by microphone 344 connected to control unit 504, microphones 414 embedded in cushion cover 400, physical proximity to sensors 510, or API 514 program commands communicated via network 502 from the user of a networked (remote) or wireless (local) multimedia peripheral device. In other examples, users can deliver voice commands via microphones 414 embedded in cushion cover 400 that is connected to via wired or wireless means to control unit 504. In further examples, microphones 344 attached to control unit 504 or microphones 414 embedded in cushion cover 400 that are connected to control unit 504 can capture audible sounds, voices, noises, and the like for transmission to a database storing sleep data record 518 or networked multimedia peripheral device operating the API 514. In still further examples, captured audio such as coughing, sneezing, moaning or crying may trigger an alert message or notification to be interpreted by analysis module 512 and delivered to a networked multimedia peripheral device operating API 514. In some embodiments, users can receive sounds, voice, audible tones, music and the like via speakers 346 connected to control unit 504 or speakers 416 embedded in cushion cover 400 connected to control unit 504.

FIG. 9 depicts sleep experiential data 540 generated by sleep analytics system 500. In some embodiments, sleep experiential data 540 is displayed on a local or remote networked multimedia peripheral device using API 514. In other embodiments, sleep experiential data 540 is displayed on control unit 504. In still other embodiments, sleep experiential data 540 is rendered from machine learning and artificial intelligence algorithms managed by analysis module 512. In some examples, sleep experience information, sleep quality metrics, behaviors, influencers, and associated ratings or values are presented in informational formats including but not limited to alphanumerical values, charts, calendars, histograms, sensor values, device setting values, physiological information, behavioral information, activity level measurements, audio files, sleep quality factors list, notification lists, recommendation lists and the like. In further embodiments, sleep experiential data 540 is generated and recorded throughout a user's sleep period. In still further embodiments, a user's cumulative or historical sleep profile data 540 may be accessed by analysis module 512 for reference during the user's sleep period for comparative analytics applications using machine learning and artificial intelligence programs. In still yet other embodiments, via network 502, analysis module 512 may access a generic or anonymized sleep profile user database of specific groups based on demographics or sleep related issues for comparative analysis and delivering recommendations for improving sleep quality. In some examples, analysis module 512 may make determinations of user sleep status, conditions, and probable sleep quality outcomes. In other examples, analysis module 512 may make recommendations on user sleep quality related to sleep routine, sleep habits, sleep conditions, physical ailments, demographic factors, stress factors, sleep partners, and the like.

The foregoing descriptions of specific embodiments of the present inventions have been presented for purposes of illustration and description. The images, drawings, schematics and etc. are not meant to be exhaustive or to limit the invention to the precise forms or scope disclosed, and many modifications and variations are possible in light of the above teaching to an individual skilled in the relevant art. Therefore, the descriptions herein are included to illustrate the operation of preferred embodiments and are not meant to limit the scope of the invention, but rather they are intended to explain the principles of the invention, utility of the innovation in specific use cases, and practical applications for various embodiments. Based on the present teachings, others skilled in the art would be capable of incorporating many minor modifications that are anticipated within this disclosure. It is intended that the scope of the invention be defined by the claims appended hereto and their equivalents. Therefore, the scope of the invention is to be broadly limited only by the following claims.

What is claimed:

1. A modular bed sheet system, comprising: a multi-layered fitted sheet comprised of a water absorbing layer, water proof layer, support layer, technical layer wherein the technical layer is a sleep management and monitoring apparatus comprised of sensors, hardware, and user control components and embedded coupling channel layer that is configured for attachment to a mattress; at least two multi-layered modular panels comprised of a water absorbing layer, water proof layer, support layer, technical layer wherein the technical layer is a sleep management and monitoring apparatus comprised of sensors, hardware, and user control components and coupling channel configured for attachment to the fitted sheet according to a specific length and width sizing; at least one multi-layered cushion cover comprised of a water absorbing layer, water proof layer, support layer, technical layer wherein the technical layer is a sleep management and monitoring apparatus comprised of sensors, hardware, and user control components and coupling channel configured for attachment to the fitted sheet; at least one anchor coupling and releasing mechanism capable of connecting and disconnecting a modular panel and cushion cover to and from the fitted sheet via a coupling channel; wherein the at least two multi-layered modular panels establish at least one independent sleep zone for each bed occupant a control unit in communication with the technical layers; wherein the control unit functions to create different component settings in separate sleep zones in the at least two multi-layered modular panels.

2. The modular bed sheet system of claim 1, wherein dimensions of the fitted sheet and attachment apparatus conforms to a specific mattress size.

3. The fitted sheet of claim 1, wherein the embedded coupling channels are configured in horizontal, vertical, and diagonal patterns, and combinations thereof.

4. The fitted sheet of claim 1, wherein the embedded coupling channels are configured with reinforced holes in intermittent patterns constructed for regular coupling and releasing of anchors connecting modular panels to the fitted sheet.

5. The modular bed sheet system of claim 1, wherein a plurality of interchangeable modular panels are coupled to the fitted sheet such that independent sleep zones are established for each bed occupant.

6. The modular bed sheet system of claim 1, wherein a plurality of interchangeable modular panels are coupled to the fitted sheet in arrangements according to:
   a. mattress size;
   b. panel size;
   c. number of panels;
   d. head box location for each sleep zone;
   e. foot box location for each sleep zone;
   f. longitude and latitude configuration of the panel on the mattress; and
   g. coupling channel connections.

7. The modular bed sheet system of claim 1, wherein modular panels forming a single sleep zone may accommodate two or more occupants.

8. The modular bed sheet system of claim 1, wherein at least one layer of the fitted sheet and modular panel is:
   a water absorbing layer is comprised of moisture absorbing and moisture wicking materials;
   a water proof layer is comprised of moisture repellant materials;

a support layer is comprised of fabricated synthetic or textile materials;

a foot panel comprised of odor absorbing materials.

9. The modular panel of claim 1, wherein the modular panel is configured in a multi-layered bag or sack architecture with a quick access mechanism for ingress and egress of occupants.

10. The modular bed sheet system of claim 1, wherein the technical layer is a sleep management and monitoring apparatus comprised of sensors, hardware, and user control components.

11. The apparatus of claim 10, wherein the components monitor and adjust independent sleep zone conditions according to direct or passive occupant inputs such as heart rate levels, body temperature, skin moisture, breathing rate, brain waves, physical movements, audible speech, and voice commands, said conditions including: heating; cooling; light levels in a room; and audio levels in sleep zone.

12. The apparatus of claim 10, wherein the components monitor and adjust independent sleep zone conditions including heating, cooling, light and audio levels based on environmental inputs including: room temperature; time of day; audible sounds; light levels in the room.

13. The apparatus of claim 10, wherein the components determine sleep quality for occupants in respective sleep zones by analyzing hardware settings, sleep zone settings, physiological data, behavioral data, environmental conditions, and user habits.

14. The anchor coupling and releasing mechanism of claim 1, wherein the mechanism is comprised of anchor hardware and fastening material that enables attaching and detaching of modular panels and fitted sheets.

15. A method of attaching and detaching of modular panels and fitted sheets according to claim 1, comprising: fastening material, comprised of durable and elastic properties, affixed to anchor hardware; and anchor hardware, comprised of durable material in shapes suitable for fastening materials; and permanently or temporarily attaching anchor hardware to fastening material, such that combined they operate to connect the modular panel and fitted sheet.

16. The method of claim 15, wherein fastening material is permanently attached to a modular panel on a first side, and permanently attached attaching anchor hardware on a second side opposite the first side, such that the anchor may be threaded through the coupling channel of the fitted sheet.

17. The method of claim 15, wherein anchor hardware is permanently attached on both sides of the fastening material, such that the anchors may be threaded through the coupling channel of the modular panel and fitted sheet.

18. The method of claim 15, wherein zipper material is permanently attached to both modular panel and fitted sheet, such that both components are connected when the respective teeth from both sides pass through a slider to form a chain.

19. The method of claim 15, wherein anchor hardware is sized and configured such that multiple anchors may be threaded through the coupling channel of the modular panel and fitted sheets simultaneously.

* * * * *